United States Patent [19]

Diaz et al.

[11] Patent Number: 4,581,168

[45] Date of Patent: Apr. 8, 1986

[54] SYNTHESIS OF HPGRF (SOMATOCRININ) IN LIQUID PHASE AND INTERMEDIATE PEPTIDES

[75] Inventors: Joseph Diaz, Perols; Henri Demarne, Montpellier; Roméo Roncucci; Paul-Henry Schmelck, both of Paris, all of France

[73] Assignee: Sanofi, Paris, France

[21] Appl. No.: 580,287

[22] Filed: Feb. 17, 1984

[30] Foreign Application Priority Data

Feb. 21, 1983 [FR] France ................................ 83 02781
Nov. 29, 1983 [FR] France ................................ 83 19058

[51] Int. Cl.$^4$ .......................................... C07C 103/52
[52] U.S. Cl. ............................................. 260/112.5 R
[58] Field of Search ................................ 260/112.5 R

[56] References Cited

U.S. PATENT DOCUMENTS

| 3,870,694 | 3/1975 | Fujino et al. | 260/112.5 R |
| 3,972,859 | 8/1976 | Fujino et al. | 260/112.5 R |
| 4,337,194 | 6/1982 | Diaz et al. | 260/112.5 R |
| 4,466,918 | 8/1984 | Birr et al. | 260/112.5 R |
| 4,476,116 | 10/1984 | Anik | 260/112.5 R |

OTHER PUBLICATIONS

Immer et al., *Helvelica Chemica Acta*, vol. 57, 1974, pp. 730-734.
*Chemical Abstracts*, vol. 98, 103 (1983), Abst. No. 101522a.
Chemical Abstract, vol. 98, 1983, p. 102, No. 101520y, Columbus, Ohio, USA, W. B. Wehrenberg et al.: "Somatocrinin Growth Hormone Releasing Factor, Stimulates Secretion of Growth Hormone in Anesthetized Rats" & Biochem. Biophys. Res. Commun. 1982, 109(2), 382-7.
Chemical Abstracts, vol. 99, 1983, p. 111, No. 64726t, Columbus, Ohio, USA, E. F. Adams et al.: "Pancreatic Growth Hormone Releasing Factor Stimulates Growth Hormone Secretion by Pituitary Cells" & Lancet 1983, 1(8333), 1100-1.
Unlisted Drugs, vol. 35, No. 3, Mar. 1983, p. 41, No. o: hpGRF & Science 218:585, 5.11.1982.
Chemical Abstracts, vol. 98, No. 13, Mar. 28, 1983, Ref. No. 101517c, p. 102, Columbus, Ohio (US) & Science (Washington D.C., 1883), 585-7 Guillemin Roger et al.; "Growth Hormone-Releasing Factor from a Human Pancreatic Tumor that Caused Acromegaly".
Nature, vol. 300, No. 5889, Nov. 18, 1982, MacMillan Journals Ltd., Basingstoke (GB) J. Rivier et al.; "Characterization of a Growth Hormone Releasing Factor from a Human Pancreatic Islet Tumour", pp. 276-278.
Chemical and Pharmaceutical Bulletin, vol. 31, No. 5, May 1983, Tokyo (JP) Haruaki Yabima et al.: "Solution Synthesis of a Tetratetracontapeptide Amide with Growth Hormone Releasing Activity", pp. 1800-1802.

*Primary Examiner*—Delbert R. Phillips
*Assistant Examiner*—F. T. Moezie
*Attorney, Agent, or Firm*—Stevens, Davis, Miller & Mosher

[57] ABSTRACT

The invention relates to synthesis of hpGRF (Somatocrinin) in liquid phase and to intermediate peptides, comprising:—coupling, one after the other and in the order of the sequence of the GRF, the fragments in which: (a) the side acid functions of the aspartic and glutamic acids and the side amine function of the lysine are protected by protector groups stable in the conditions of deprotection of the group Boc, (b) the guanidine function of the arginine is protected by protonation, and (c) the N-terminal amino acid is protected on the amine by the Boc group;—selectively eliminating the group Boc from the N-terminal amine of the peptide in phase of elongation by hydrolysis with trifluoroacetic acid, said coupling being effected in an aprotic polar solvent and—eliminating, at the end of sequence, all the protector groups by hydrolysis with the aid of a 0.1 to 1M solution of methanesulfonic or trifluoromethanesulfonic acid in trifluoroacetic acid.

7 Claims, No Drawings

SYNTHESIS OF HPGRF (SOMATOCRININ) IN LIQUID PHASE AND INTERMEDIATE PEPTIDES

The present invention relates to a synthesis of hpGRF (Somatocrinin) in liquid phase and intermediate peptides.

hpGRF (human Pancreatic Growth Hormone releasing Factor) or Somatocrinin is a peptide constituted by the chain formation of 44 amino acids. Its sequence is as follows:

```
     1                       5
H—Tyr—Ala—Asp—Ala—Ile—Phe—Thr—Asn—Ser—

10                      15
 —Tyr—Arg—Lys—Val—Leu—Gly—Gln—Leu—Ser—Ala—

20                      25
 —Arg—Lys—Leu—Leu—Gln—Asp—Ile—Met—Ser—

30                      35
 —Arg—Gln—Gln—Gly—Glu—Ser—Asn—Gln—Glu—

40           44
             —Arg—Gly—Ala—Arg—Ala—Arg—Leu—NH2
```

It has recently been discovered by A. GUILLEMIN et coll. (Science, 218, 585–587 (1982) from extracts of a human pancreatic tumour.

This peptide is particularly active on the stimulation of the release of the growth hormone (GH) both in vitro and in vivo. In vitro, in particular, its effectiveness is shown at doses of some fento moles/ml ($ED_{50}=15$ fento moles/ml). The therapeutic interest of this substance in human medicine will therefore lie in the treatment of dwarfism and retarded growth in pediatrics. Other applications are possible in the cases of anabolic protein deficiency (stress-related ulcers, repair of fractures or of wounds of the cartilage, extensive burns (during the anabolic phase), cutaneous repairs, osteoporoses).

In the veterinary domain, the interest of this compound in the weight growth of farm-breeding animals (beef-cattle, sheep, pigs, chicken, . . . ) and in the increase in lactation (cows, ewes) is obvious.

The industrial development of this polypeptide compound necessitates the synthesis of large quantities of this substance. Conventional processes of synthesis in solid phase allow small quantities of this active principle to be prepared in short periods of time (Science, 218, 585–587 (1982) but at very high costs which are incompatible with a large-scale pharmaceutical development.

The present invention describes a process of synthesis in liquid phase which may be carried out on an industrial scale, allowing access to the active principle with excellent yield and rate of purity. This process is based on the principle of synthesis by fragments.

The process of the present invention is characterized by the step of coupling, one after the other and in the order of the sequence, the fragments in which:

(a) the side acid functions of the aspartic and glutamic acids and the side amine function of the lysine are protected by protector groups stable in the conditions of deprotection of the Boc group (tertiobutoxycarbonyl), (b) the guanidine function of the arginine is protected by protonation, and (c) the N-terminal amino acid is protected on the amine by the Boc group, (d) by selectively eliminating the Boc group from the N-terminal amine of the peptide in elongation phase by hydrolysis with trifluoroacetic acid, said coupling being effected in an aprotic polar solvent, and at the end of sequence all the protector groups are eliminated by hydrolysis with the aid of a 0.1 to 1M solution of methanesulfonic or trifluoromethanesulfonic acid in trifluoroacetic acid.

The process of the present invention may also be applied to the synthesis of hpGRF-1-40, a natural product also isolated by R. GUILLEMIN, which is almost as active as the hpGRF-1-44 and able to be used in the same therapeutic applications.

The process of synthesis of the GRF is further characterized by the following features:

Application of the principle of minimum protection to the functionalized side chains.

Temporary protection of the side guanidine function of the arginine by the nitro group. The arginine is introduced in sequence in the nitro guanidine form. The nitro function is then eliminated as soon as possible by catalytic hydrogenation with the aid of Pd/charcoal, or by using in place of gaseous hydrogen a generator of hydrogen such as formic acid or ammonium formate. In this way, all the synthesized fragments possessing arginine in their sequence have, at the end of synthesis, the guanidine functions simply protected by protonation with the aid of a strong acid (hydrochloric acid, for example).

The carboxylic acid functions of the side chains of the glutamic and aspartic acid are protected by groups cleavable by catalytic hydrogenation ($H_2$/Pd/ charcoal) or in a strong acid medium such as the methanesulfonic acid (0.5 M)—trifluoroacetic acid, or trifluoromethanesulfonic acid (0.5 M)—trifluoroacetic acid mixtures. The invention recommends as protectors benzyl (O Bzl) or 2,6 dichlorobenzyl ester. These protector groups are stable in the conditions of intermittent deprotection of the amines in alpha (elimination of the t-butyloxycarbonyl (Boc) groups by trifluoroacetic acid).

The amine functions of the side chains of the lysines are protected by groups cleavable under the same conditions as previously. The invention recommends the benzyloxycarbonyl (Z), 2-chloro or 2-bromo benzyloxycarbonyl (2-Cl or 2-Br Z) groups stable in the conditions of intermittent deprotection by trifluoroacetic acid.

The hydroxyl functions present in the threonine, serine and tyrosine are not protected.

The elongation of the peptide from the synthesized fragments is effected by using as coupling agent the hexafluorophosphate of benzotriazolyl oxyphosphonium (BOP), or dicyclohexyl carbodiimide in the presence of 1-hydroxy benzotriazole, or according to the method employing carboxyazides (Curtius), in an appropriate solvent such as dimethyl formamide or dimethylsulfoxide. Isolation of the product from the reaction medium is effected by introducing a third solvent which renders insoluble (ether, ethyl acetate, . . . ) which precipitates the peptide.

One is limited during the steps of coupling to summary purifications of the solid-phase washing type with the aid of appropriate solvents in order to eliminate the slight excess of the last coupled fragment, as well as the impurities brought by the coupling agents.

Each fragment coupling operation is followed by a phase of intermittent deprotection of the Boc tertiobutoxycarbonyl protector group, at the level of the amine on which the following coupling will be effected. Such deprotection is ensured by trifluoroacetic acid in methylene chloride (50/50 by volume).

The deprotections of the side chains at the end of elongation of the peptide may be effected by hydrogenation in the presence of a catalyst (such as Pd/C) with the aid of gaseous hydrogen under a slight pressure (1 to 5 kg) or with a generator of hydrogen such as formic acid or ammonium formate. It is also possible to eliminate this type of protector group by a strong acid such as the mixtures of methanesulfonic acid in trifluoroacetic acid (0.5M) or of trifluoromethanesulfonic acid in trifluoroacetic acid (0.5M).

The product, after the terminal deprotections, is purified by filtration over Sephadex gel G 50 with the acid of 30% acetic acid. The GRF-1-44 enriched fractions are gathered together and subjected to a chromatography on ion exchangers (cations) of the carboxy type and with the aid of a gradient with increasing ionic force adapted to the type of ion exchanger resin used. The fractions of highest purity are gathered together and purified, either by partition chromatography on an appropriate support of the Sephadex G 50 or Biogel P 10 type, or by counter-current distribution.

The fractions of which the titer of purity is judged satisfactory by analytic HPLC are gathered together. The others are recycled.

A variant of the process consists in replacing the partition chromatography or counter-current distribution by preparative HPLC.

The fragments used for the synthesis of hpGRF-1-44 are determined on the basis of chemical considerations taking particular account of the minimum risks of racemization during the fragment coupling phases.

Each of the fragments is then synthesized according to a strategy adapted to each case in accordance with a step-wise process in liquid phase.

Scheme 1 hereinafter represents one of the strategies of synthesis which may be used for the synthesis of hpGRF-1-44.

The vertical arrows delimit the fragments used in the synthesis and each of them is designated by a letter:
A: fragment 40-44
B: fragment 33-39
C: fragment 28-32
D: fragment 25-27
E: fragment 21-24
F: fragment 16-20
G: fragment 12-15
H: fragment 5-11
I: fragment 1-4

In addition, the protections of the side chains have been symbolized by:
$X_1$ = ester of benzyl type (O Bzl)
$X_2$ = carbamate protection of the benzyloxycarbonyl (Z) type.

Tables I to IX thereafter indicate the process of synthesis used for each of fragments A to I.

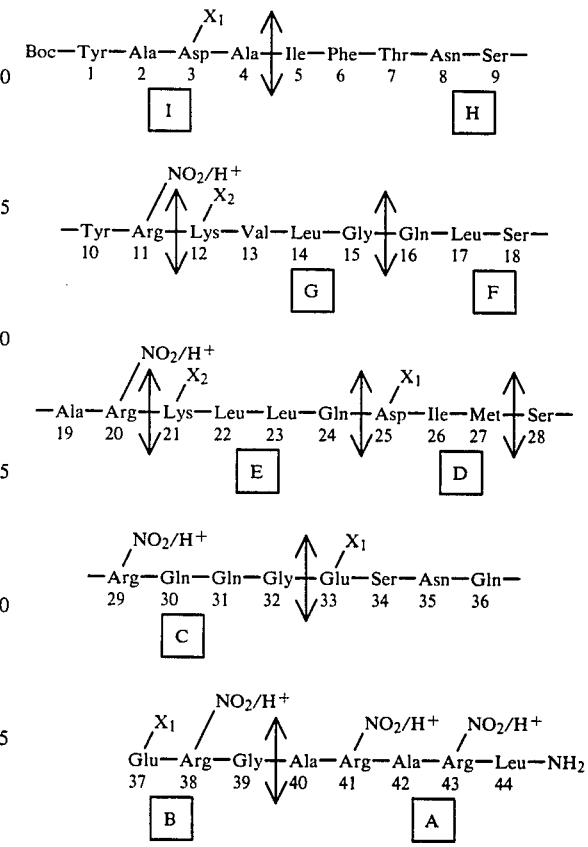

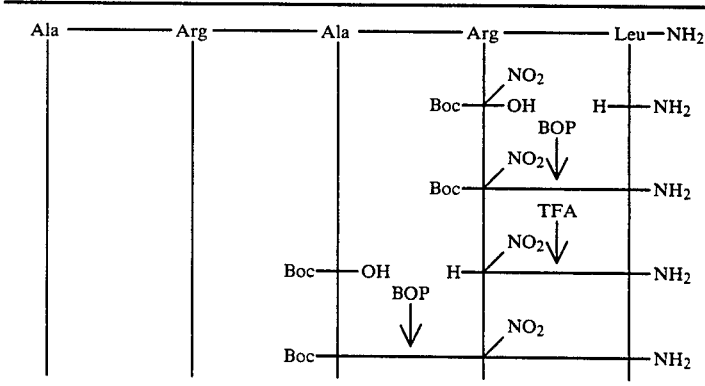

TABLE I-continued
(fragment A)
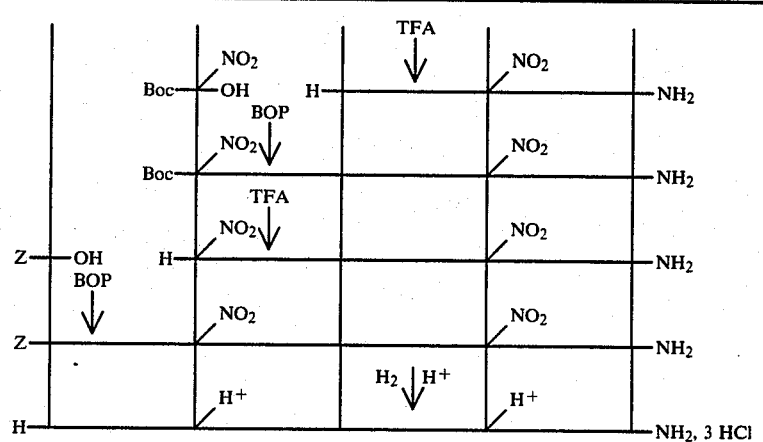
TABLE II
(fragment B)
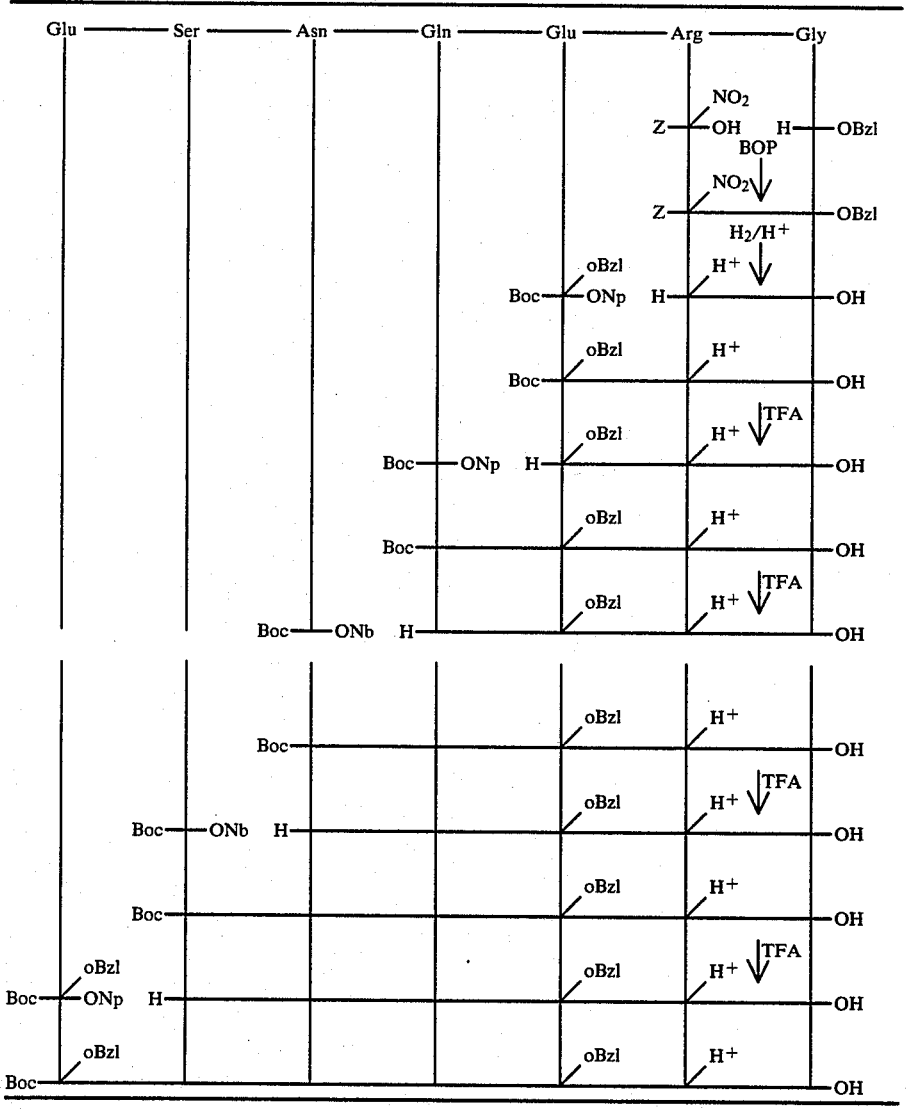

TABLE III
(fragment C)
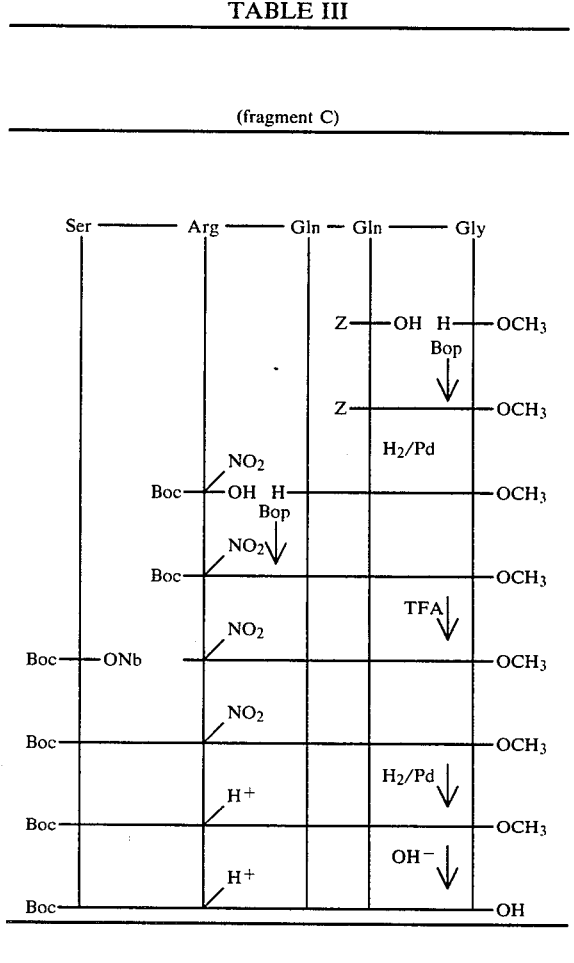
TABLE IV
(fragment D)
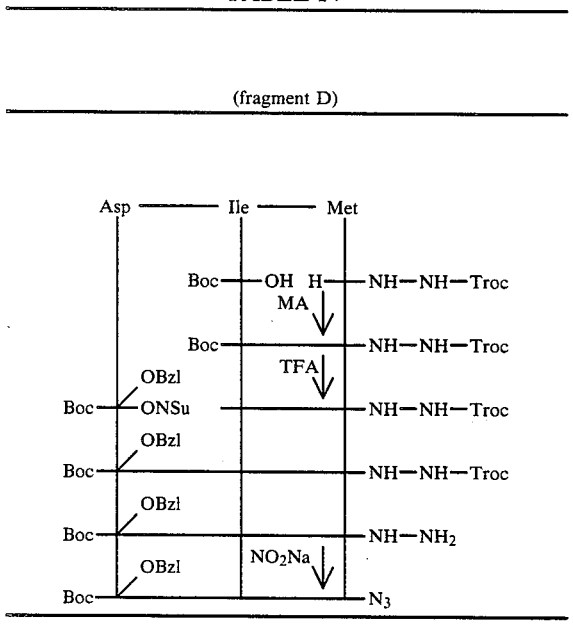
TABLE V
(fragment E)
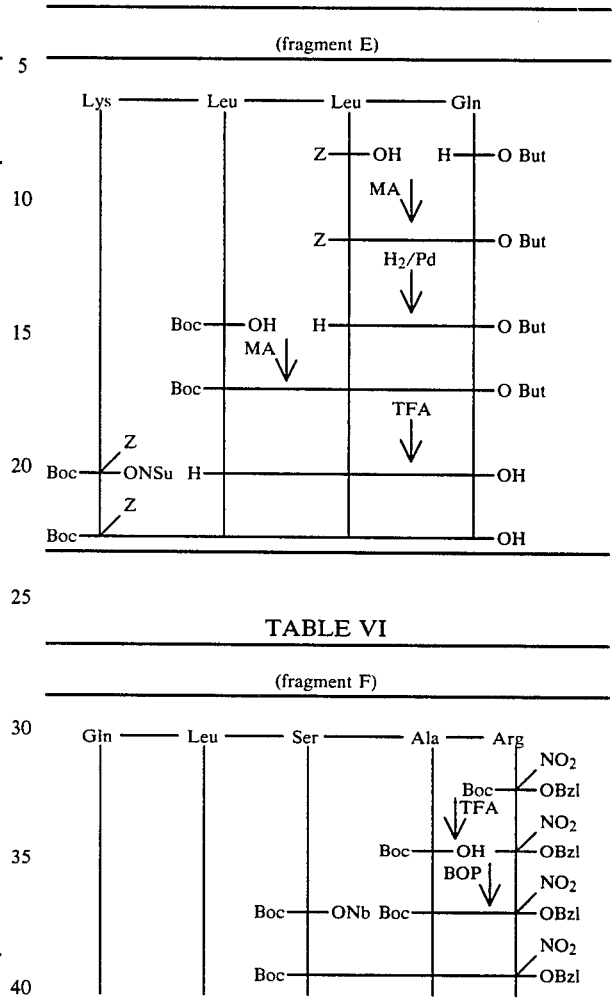
TABLE VI
(fragment F)
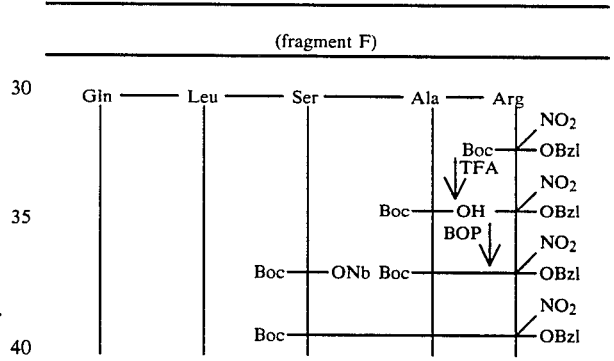
TABLE VII
(fragment G)
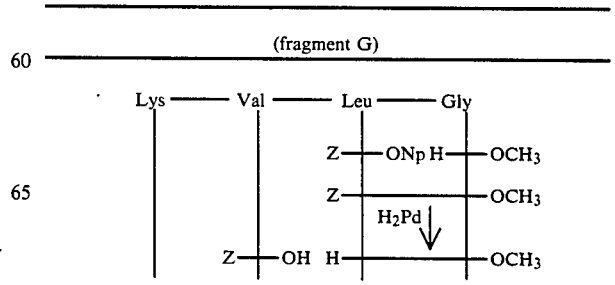

TABLE VII-continued
(fragment G)

[Synthesis scheme for fragment G showing Boc, Z protecting groups with ONp, MA, H₂/Pd, OH⁻ reagents and OCH₃, OH products]

(fragment I)

[Synthesis scheme for fragment I: Tyr—Ala—Asp—Ala with Boc, Z protecting groups; OBzl, OBu$^t$ side-chain protection; ONSu, OTcp, ONp activating groups; TFA deprotection steps]

The hpGRF-1-44 may also be prepared in accordance with a process employing the fragments:
20–44: Peptide K
5–19: Peptide J
1–4: Peptide I

TABLE VIII
fragment H

[Synthesis scheme for fragment H: Ile—Phe—Thr—Asn—Ser—Tyr—Arg with Boc protecting groups; ONp, ONb, ONSu activating groups; OBzl, NO₂ side-chain protection; BOP coupling; TFA and H₂/Pd deprotection steps]

which are coupled in the following order:
5-19+20-44: 5-44
1-4+5+44: 1-44

Peptide J and peptide K are in turn synthesized by a process by fragments.

Peptide 5-19 is synthesized from 3 fragments and peptide 20-44 from 7 fragments.

Schemes II and III hereinafter represent the strategies used for preparing peptides J and K, peptide I having already been prepared in scheme I.

Scheme IV represents the coupling of the 3 peptides I, J and K to arrive at the hpGRF 1-44.

Tables X to XV show the schemes of synthesis of the fragments not described on following scheme I.

Finally, in all cases, to obtain hpGRF 1-40, it suffices to reduce fragment A to alaninamide.

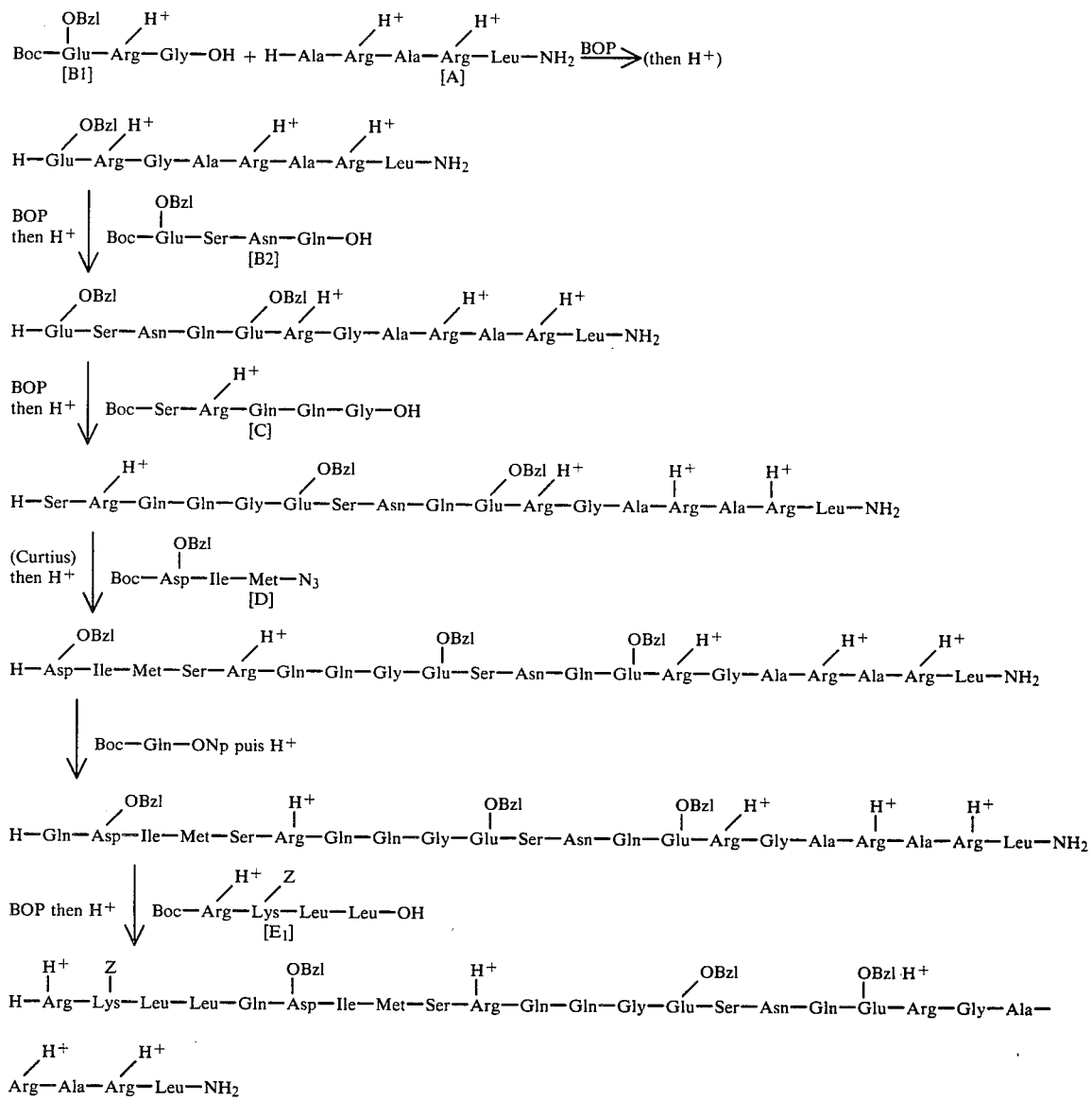

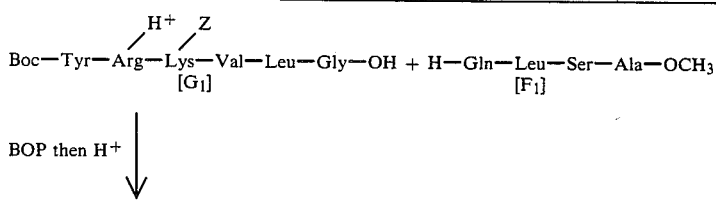

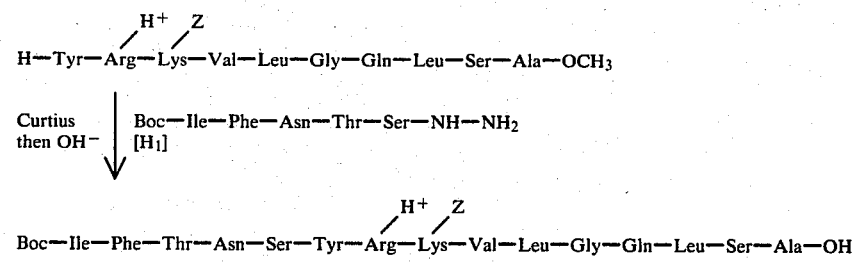
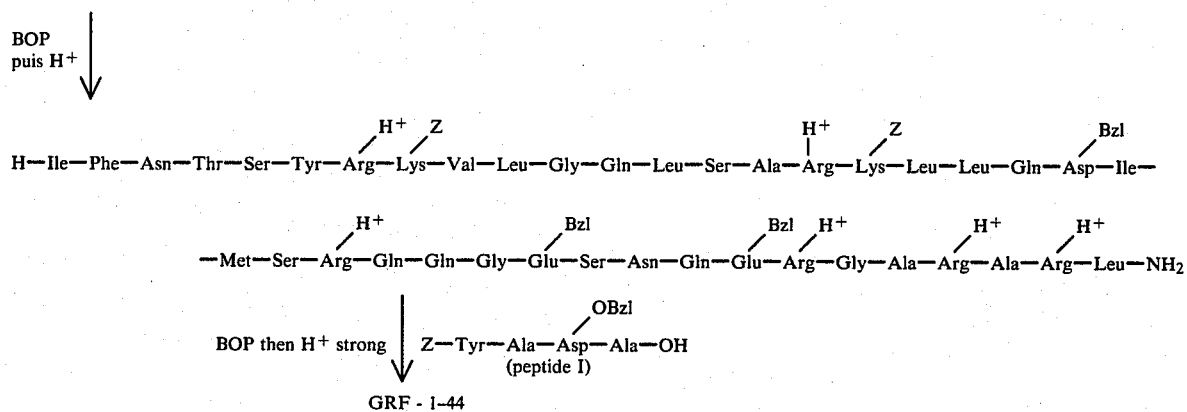
Scheme IV
PASSAGE of the SEQUENCE of GRF 1-44
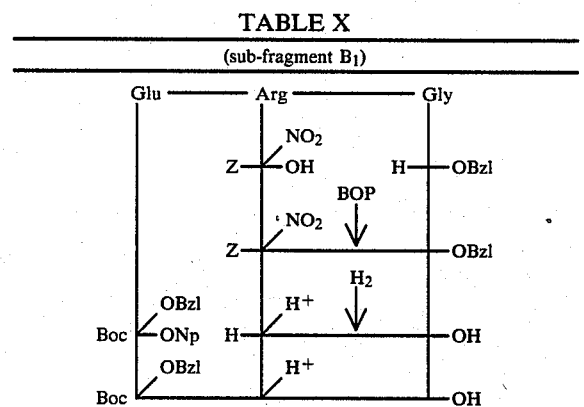
TABLE X
(sub-fragment B₁)
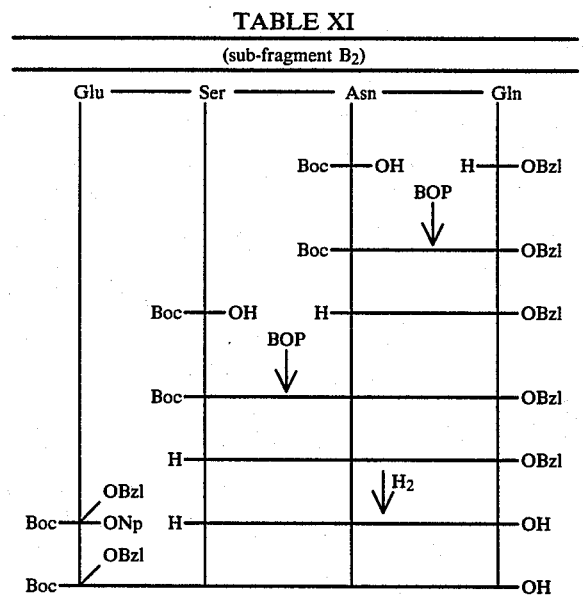
TABLE XI
(sub-fragment B₂)

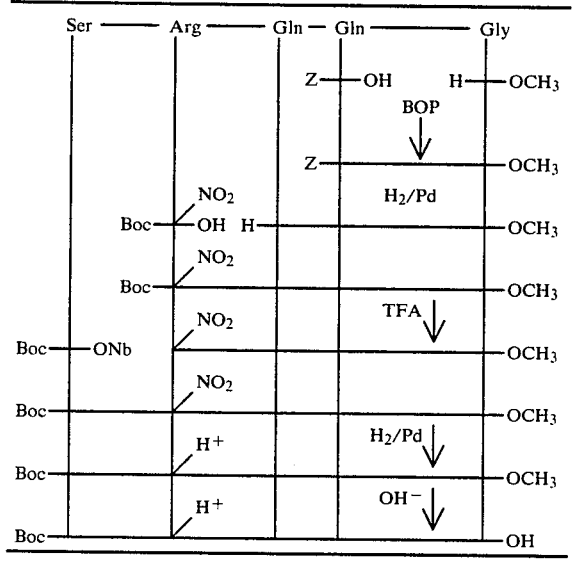
TABLE XII
(fragment E₁)
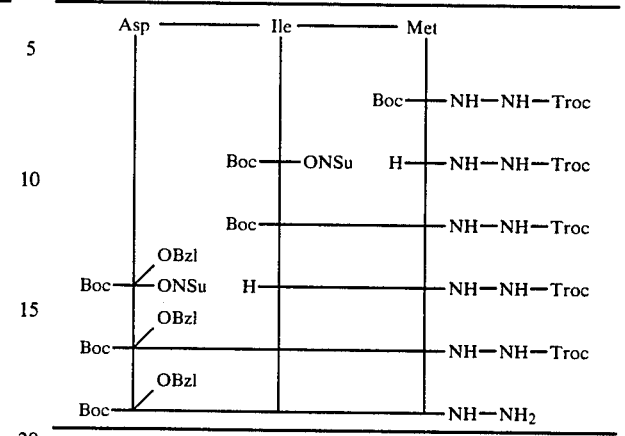
TABLE XIII
(fragment F₁)
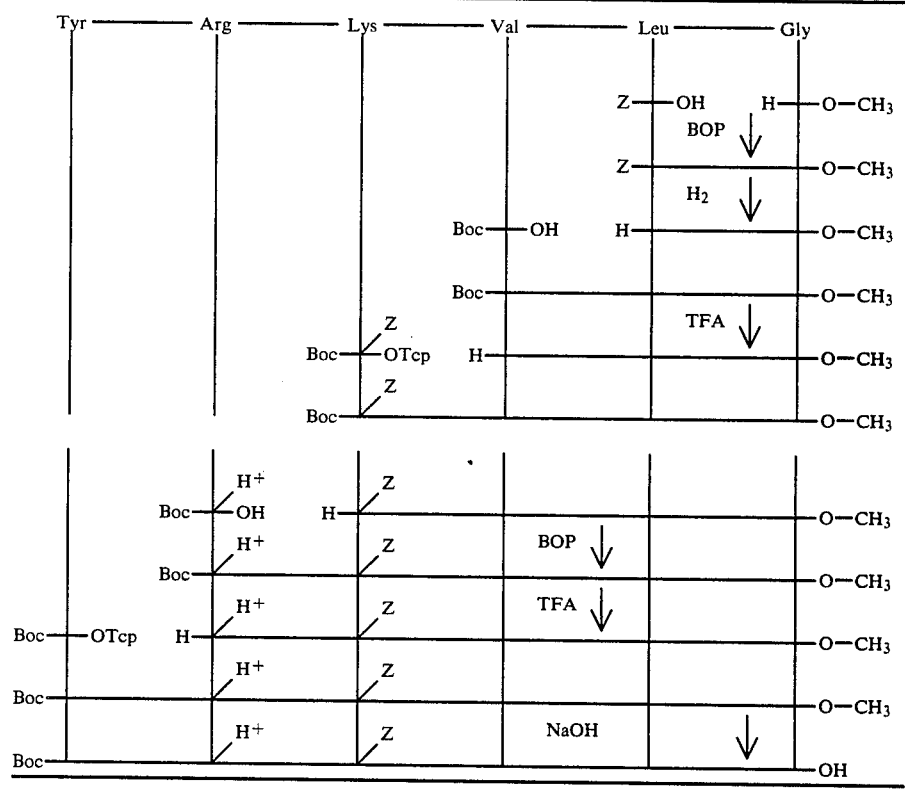
TABLE XIV
(fragment G₁)

TABLE XV (fragment H₁)

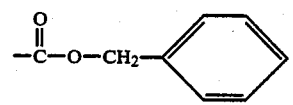

The following examples will enable the scope of the invention to be more readily understood.

The following abbreviations will be used.

The amino acids are represented by the symbols recommended by the Nomenclature Commission of the IUPAC-IUB, Biochemistry Section.

Ala: Alanine
Arg: Arginine
Asn: Asparagine
Asp: Aspartic acid
Gln: Glutamine
Glu: Glutamic acid
Gly: Glycine
Ile: Isoleucine
Leu: Leucine
Lys: Lysine
Met: Methionine
Phe: Phenyl alanine
Ser: Serine
Thr: Threonine
Tyr: Tyrosine
Val: Valine With the exception of glycine, they all have the L-configuration.

| | | |
|---|---|---|
| CCM | thin layer chromatography | |
| OBzl | benzylic ester | 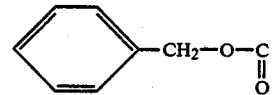 |
| Z | benzyl oxycarbonyl (carbamate) | |
| Boc | tertiobutoxycarbonyl (carbamate) | |
| DMF | dimethyl formamide | |
| NEM | N—ethyl morpholine | |
| TFA | trifluoroacetic acid | |
| MA | method of coupling with mixed anhydrides | |
| ONSU | ester activated with N—hydroxy succinimide | 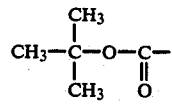 |

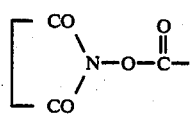

| | | |
|---|---|---|
| ONp | ester activated with ortho nitro phenol | |
| Troc | trichloro ethoxy carbonyl (carbamate) | $CCl_3-CH_2-O-\overset{\underset{\parallel}{O}}{C}-$ |
| OBu$^t$ | ester with tertiobutanol | $-\overset{\underset{\parallel}{O}}{C}-O-\overset{\underset{CH_3}{\overset{CH_3}{\mid}}}{\underset{\mid}{C}}-CH_3$ |
| OTcp | ester activated with 2,3,5 trichlorophenol | |
| OHBT | N—hydroxy benzotriazole | |
| ONb | ester activated with N—hydroxy 5-norbornene 2,3-dicarboximide | |
| BOP | hexafluorophosphate of benzo triazolyl oxyphosphonium | |
| DCHa | dicyclohexylamine | |
| DCU | dicyclohexylurea | |
| DCC or DCCl | dicyclohexylcarbodiimide | |
| TA | ambient temperature | |
| DIPEA | diisopropyl ethyl amine | |
| EPP | polypeptidic purity | |
| TFMSA | trifluoro methane sulfonic acid | |
| AAA | analysis of amino acids | |
| HPLC | high performance liquid chromatography | |

Media of chromatography expressed in volumes:

| | |
|---|---|
| BEW$_1$ | butanol, AcOH, H$_2$O 72/7/21 |
| BEW$_2$ | butanol, AcOH, H$_2$O 67/10/23 |
| BPEW$_1$ | butanol, pyridine, AcOH, H$_2$O 50/12/12/25 |
| EPAW | AcOEt, pyridine, HCO$_2$H, H$_2$O 63/21/10/6 |
| BPEW$_2$ | butanol, pyridine, AcOH, H$_2$O 42/24/4/30 |

EXAMPLE I

Synthesis of H-Ala-Arg-Ala-Arg-Leu-NH$_2$ (fragment A)

1. 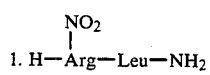

130 g of leucine amide (H-Leu-NH$_2$) are dissolved at ambient temperature in 1.5 l of DMF. 333 g of Boc-Arg(NO$_2$)-OH then 500 g of BOP are added. The pH is adjusted to 7 with pH paper (on small samples diluted with water) and with the aid of N-ethylmorpholine (NEM). The medium is stirred and the development of the reaction is followed by TLC. The reaction is terminated after 4 hours. The medium is evaporated to dryness in vacuo at 25°. The residue is taken up in 1 liter of water and solid is obtained which is washed with water, then with a 5% aqueous solution of NaHCO$_3$ with water, with ethyl acetate and, finally, the solid is dried in air. It is monitored by TLC.

The preceding solid is introduced into 2 l of a 50-50 by volume mixture of trifluoroacetic acid/methylene chloride. The medium is stirred for 10 mins. at ambient temperature and evaporated to dryness in vacuo at ambient temperature. The residue of evaporation is taken up in ether, drained, dried and monitored by TLC and NMR.

Yield: 339 g (90%) expressed in trifluoroacetate of a white solid.

2. H-Ala-Arg(NO$_2$)Leu-NH$_2$ 443 g of trifluoroacetate of H-Arg(NO$_2$)Leu-NH$_2$ are dissolved in 2 l of DMF. 200 g of Boc-Ala-OH, then 500 g of BOP are added. The pH is adjusted to 7 with pH paper (on small samples of the reaction medium) with the aid of NEM. The medium is stirred and the development of the reaction is followed by TLC. The reaction is terminated after 4 hrs. The medium is evaporated to dryness in vacuo at 25°. The residue is taken up in 2 l of water and 2 l of ethyl acetate. The organic phase is washed with a 5% aqueous solution of NaHCO$_3$, with water, dried and evaporated. The tripeptide is recrystallized in ethyl-acetate/ether, and finally dried in vacuo. It is monitored by TLC and NMR.

The preceding product, dried, is treated with a 50-50 (by volume) mixture of TFA-CH$_2$-Cl$_2$ under the conditions of the preceding Example I-1). Isolation is also effected under the same conditions.

Yield: 412 g (80%) expressed in trifluoroacetate of a white pulverulent product (monitored in TLC and NMR).

3. Arg(NO$_2$)-Ala-Arg(NO$_2$)-Leu-NH$_2$

From 515 g of H-Ala-Arg(NO$_2$)-Leu-NH$_2$ in 2.5 l of DMF and 333 g of Boc-Arg(NO$_2$)-OH and 500 g of BOP, 607 g (85%) of a white solid monitored by TLC and NMR are obtained by employing the operational conditions described in Example I-1, after treatment with the mixture TFA-CH$_2$Cl$_2$.

4. Z-Ala-Arg(NO$_2$)-Ala-Arg-Leu-NH$_2$

From 715 g of trifluoroacetate of E-Arg(NO$_2$)Ala-Arg(NO$_2$)-Leu-NH$_2$ in solution in 4 l of DMF and 233 g of Z-Ala-OH and 500 g of BOP employing the same technique as the one described in I-2 (and without treatment in that case by TFA-CH$_2$Cl$_2$), 612 g of Z-Ala-Arg(NO$_2$)-Ala-Arg(NO$_2$)Leu-NH$_2$ (76%) are obtained, after recrystallization in the DMF-ether mixture, in the form of a white pulverulent solid, monitored by TLC and NMR.

5. Ala-Arg-Ala-Arg-Leu-NH$_2$, 3 HCl 200 g of Z-Ala-Arg(NO$_2$)Ala-Arg(NO$_2$)-Leu-NH$_2$ (0.25 mole) are suspended in 2 l of methanol containing 0.8 mole of HCl. 40 g of Pd/C with 10% of Pd are added, and the medium is stirred in an atmosphere of hydrogen under a pressure of 1.2 bars, for 24 hours. After this interval of time, the end of the reaction is monitored by TLC. The catalyst is eliminated by filtration and the solvent is evaporated in vacuo at ambient temperature.

The solid residue is purified by chromatography over silica gel, using an elution medium the (50-12-12-25 by volume) mixture of butanol, pyridine, HO$_2$CCH$_3$, OH$_2$.

The fractions containing the pure product are collected together, evaporated and lyophilized.

Yield: 119 g (69%) of a white pulverulent solid Monitored by: NMR, TLC.

Analysis of aminoacids: Leu 1.03 (1), Arg 1.92 (2), Ala 1.95 (2).

EXAMPLE II

Synthesis of Boc-Glu(OBzl)-Arg-Gly-OH, HCl (fragment B$_1$)

1. Z-Arg(NO$_2$)-Gly-OBzl 3.37 g (0.01 mole) of tosylate of H-Gly-OBzl are dissolved in 15 ml of DMF, then 1 equivalent of NEM (1.3 ml) is added. This solution is added to a solution of 3.53 g (0.01 mole) of Z-Arg(NO$_2$)-OH in 15 ml of DMF containing 1 equivalent of NEM (1.3 ml). 4.5 g (0.01 mole) of BOP are then added to the reaction mixture whose pH is then brought to 7 by addition of NEM and which is stirred at ambient temperature for 2 hours 30 minutes (the end of the reaction is determined by TLC: chloroform-methanol (3/1).

The reaction mixture is evaporated to dryness under reduced pressure (0.1 mm of mercury) at a temperature lower than 30° C. The residue is taken up in 100 ml of ethyl acetate. This solution is poured into 120 ml of strongly stirred iced water. After a few instants of stirring, a precipitate is formed which is left overnight in the refrigerator.

The solid is drained and washed successively in the solid state with:
- 2×100 ml of an aqueous solution of sodium bicarbonate
- 2×100 ml of a 5% aqueous solution of SO$_4$HK-SO$_4$K$_2$
- 2×100 ml of water
- 2×100 ml of ether then dried in vacuo (0.1 mm of mercury) up to a constant weight.

Yield: 4 g (80%) Koffler melting point: 149° C. TLC: chloroform-methanol (3/1) Rf: 0.73 Monitored by NMR.

2. HCl-H-Arg-Gly-OH 100 g (0.2 mole) of Z-Arg(NO$_2$)-Gly-OBzl are suspended in a mixture of 600 ml of water, 600 ml of N hydrochloric acid and 100 ml of tetrahydrofuran. 60 g of 10% Pd/C containing 50% humidity are added. This mixture is hydrogenated for 48 hours at ambient temperature and under a pressure of 15 mm of mercury. The catalyst is then filtered and the aqueous solution is taken to pH 6.5 by addition of amberlite IR 45 resin (OH form). The resin is drained. The solution is then taken to pH 8.5 by addition of a fresh quantity of resin and the whole is stirred for 20 minutes in a rotavapor in vacuo (25 mm of mercury). The resin is drained and the absence of ammonium chloride in the aqueous solution is checked by the Nesler test, then this solution is evaporated to dryness under reduced pressure (0.1 mm of mercury) at a temperature lower than 30° C. A gummy residue is obtained which is dried overnight in a desiccator with phosphoric anhydride.

Yield: 43.19 g (80.6%) TLC: ethyl acetate-pyridine-formic acid-water (40-21-10-6) Rf: 0.1 Sakaguchi test positive (red spot) Monitored by NMR.

3. Boc-Glu(OBzl)-Arg(HCl)-Gly-OH 41.5 g of HCl-H-Arg-Gly-OH (0.155 mole) are dissolved in a mixture of 400 ml of DMF and of 130 ml of water. The pH is adjusted to 7 by addition of N hydrochloric acid.

To this solution are simultaneously added:
- a solution of 68.8 g of Boc-Glu(OBzl)-ONP (0.150 ml) in a mixture of 100 ml of DMF and 40 ml of water.
- a solution of 22.7 g of hydroxybenzotriazole (0.150 mole) in a mixture of 100 ml of DMF and 40 ml of water.
- a solution of 37.8 ml of NEM (2×0.150 mole) in 100 ml of DMF.

The reaction mixture is stirred at ambient temperature and the reaction is followed in TLC (chloroform-methanol-acetic acid 95-5-9 and pyridine-ethyl acetate-formic acid-water 21-40-10-6).

After one hour of reaction, 13.76 g of Boc-Glu(OBzl)-ONP are added.

After 2 hours of reaction, 13.76 g of Boc-Glu-OBzl)-ONP are added.

After 3 hours of reaction, 7 g of Boc-Glu(OBzl)-ONP are added and the reaction is continued for 1 hour.

The reaction mixture is then evaporated to dryness under reduced pressure (0.1 mm of mercury) and at a temperature lower than 30° C. A thick oil is obtained which is dissolved in 500 ml of ethyl acetate. By addition of 1 liter of ether, a thick oil is formed. It is left to stand 24 hours in the refrigerator, then the liquid phase is decanted.

The residual oil is taken up in 500 ml of methanol. To this solution are added 500 g of silica (70-230 mesh) and the solvent is evaporated by means of a rotavapor. The powder obtained is mixed with a 80-20 mixture of chloroform-methanol and the gel formed is introduced at the top of a column of silica gel (height 200 cm, diameter 85 mm) mounted in the 80-20 chloroform-methanol mixture.

The product is eluted with:
80-20 mixture of chloroform-methanol: 25 liters.
50-50 mixture of chloroform-methanol: 10 liters
methanol: 30 liters.

The purification is followed by TLC (pyridine-ethyl acetate-formic acid-water, 21-40-10-6)
2 fractions are collected:
fraction A, 29.80 g
TLC: pyridine-ethyl acetate-formic acid-water, 21-40-10-6; Rf: 0.75
Monitored by NMR
HPLC—EPP: 96.98%
AAA: Glu 1.01-Gly 1.01-Arg 0.98
Fraction B, 36.82 g
TLC: pyridine-ethyl acetate-formic acid-water, 21-40-10-6; Rf: 0.75
1H NMR spectrum conformable
HPLC—EPP: 99.61%
AAA: Glu 0.93-Gly 0.99-Arg 1.08

EXAMPLE III

Synthesis of Boc-Glu(OBzl)-Ser-Asn-Gln-OH (fragment B2)

1. Boc-Asn-Gln-OBzl

TFA, H-Gln-OBzl (0.445 mole) are dissolved in 500 ml of DMF. To this solution are successively added:
103.3 g of Boc-Asn-OH (0.445 mole)
62.3 ml of NEM
217.8 g of BOP (0.5 mole)
then the pH of the solution is returned to 7 by addition of NEM.

The mixture is stirred at ambient temperature, the pH is maintained at 7 by addition of NEM if necessary. The reaction is followed in TLC (3-1 chloroform-methanol). After one hour, the reaction is terminated and the product is precipitated by addition of 1.5 liters of ethyl acetate. It is left one hour with stirring then left overnight in the refrigerator.

The solid is drained, washed with ethyl acetate (3×500 ml), with ether (1 liter), then dried.
Yield: 108.13 g (53.9%),
TLC: 3-1 chloroform-methanol; Rf: 0.63.

2. TFA, H-Asn-Gln-OBzl 102 g of Boc-Asn-Gln-OBzl (0.226 mole) are dissolved in 500 ml of TFA cooled in a bath of ice. The bath of ice is removed and stirring is continued at ambient temperature for 15 minutes. A light insoluble substance is drained and stirring is continued for 15 minutes. The reaction medium is concentrated to ¼ under reduced pressure (25 mm of mercury) and is taken up in 300 ml of ether. This operation is repeated twice (2×300 ml of ether) and the remaining solvent is eliminated in vacuo (25 mm of mercury).

A hygroscopic white solid is obtained.

Yield: 107 g, TLC: 3-1 chloroform-methanol; Rf: 0.08.

3. Boc-Ser-Asn-Gln-OBzl 0.226 mole of TFA, H-Asn-Gln-OBzl is dissolved in 1.5 liters of DMF. To this solution are successively added:
48.4 g of Boc-Ser-OH, ½ H₂O (0.226 mole)
34.8 ml of NEM (0.27 mole)
111 g of BOP (0.25 mole)
then the pH of the solution is returned to 7 by addition of NEM.

The mixture is stirred at ambient temperature, maintaining the pH at 7 by addition of NEM if necessary. The development of the reaction is followed in TLC (chloroform-methanol-acetic acid, 9-2-0.5). After 2 hours, the reaction is terminated. A light insoluble substance is filtered and the reaction medium is evaporated to dryness under reduced pressure (0.1 mm of mercury) at a temperature lower than or equal to 30° C.

The residual oil is taken up in 800 ml of ethyl acetate. It is left for 1 hour with stirring then left overnight to stand in a refrigerator.

The solid is drained, washed with ethyl acetate (2×200 ml) then with ether (200 ml) and dried in vacuo.
Yield: 108.32 g (89%), TLC: chloroform-methanol-acetic acid, 9-2-0.5; Rf: 0.42.

4. TFA, H-Ser-Asn-Gln-OBzl 108 g of Boc-Ser-Asn-Gln-OBzl (0.2 mole) are dissolved in 520 ml of TFA cooled in an ice bath. The ice bath is removed and the product is stirred for 30 minutes at ambient temperature. A light insoluble substance is filtered, then evaporated to dryness under reduced pressure at a temperature lower than 30° C. The residue is taken up in ether, the solid is drained, washed several times with ether and dried.
Yield: 139° C., TLC: tetrahydrofuran-pyridine-formic acid-water, 60-20-10-6; Rf: 0.81.

5. TFA, H-Ser-Asn-Gln-OH 0.2 mole of TFA, H-Ser-Asn-Gln-OBzl are dissolved in 1 liter of water. 22.4 g of 10% Pd/C containing 50% humidity are added to the solution. The mixture is hydrogenated at ambient temperature and under a pressure of 15 mm of mercury for 24 hours with stirring. The catalyst is filtered then evaporated to dryness under reduced pressure (0.1 mm of mercury) and at a temperature lower than 30° C. The residue is left to dry overnight in a desiccator with phosphoric anhydride.
Yield: 93.66 g, TLC: tetrahydrofuran-pyridine-formic acid-water, 60-20-10-6; Rf: 0.45.

6. Boc-Glu(OBzl)-Ser-Asn-Gln-OH 0.2 mole of TFA H-Ser-Asn-Gln-OH are dissolved in a mixture of 100 ml of water and of 600 ml of DMF. The pH of the solution is taken to 7 by addition of NEM and a solution of 87.11 g of Boc-Glu(OBzl)-ONP (0.19 mole) in 600 ml of DMF then 29.5 g of HOBT (0.19 mole) is added. The pH of the mixture is returned to 7 by addition of NEM and it is stirred at ambient temperature: after one hour of stirring, 2.7 g of Boc-Glu(OBlz)-ONP are added.

The reaction is followed in TLC (tetrahydrofuran-pyridine-formic acid-water, 60-20-10-6 and chloroform-methanol-acetic acid, 95-5-3).

Half an hour after the last addition, a light insoluble substance is filtered, then evaporated to dryness under reduced pressure (0.1 mm of mercury) at a temperature lower than 30° C. The oil obtained is taken up in 800 ml of ethyl acetate, a slightly gelatinous precipitate is formed. It is drained and washed with ethyl acetate (2×400 ml), then with ether and dried.

Yield: 114.3 g (90%).

The product must be washed again with ethyl acetate (1.2 liters) with stirring for 4 hours at ambient temperature. The solid is drained, washed with ether, dried.

Yield: 95.85 g (71.9%), TLC: tetrahydrofuran-pyridine-formic acid-water, 60-20-10-6, Rf: 0.62.

n butanol-pyridine-acetic acid-water, 50-12-12-25-Rf: 0.46

1 H NMR, conformable
HPLC-EPP 87.81
AAA: Asn(asp): 1.01-Ser: 0.89-Glu(gln): 2.05
Melting point (Koffler): 134° C. dec.

EXAMPLE IV

Synthesis of Boc-Ser-Arg-Gln-Gln-Gly-OH, HCl (fragment C)

1. Z-Gln-Gly-OMe

A suspension, cooled on an ice bath, of 75.36 g of HCl, H-Gly-OMe (0.6M) in one liter of DMF has 168.2 g of Z-Gln-OH (0.6), 256.41 g of BOP (0.7M) and 165.4 ml of N-ethyl morpholine (1.3M) added thereto. After 20 hours of reaction at ambient temperature, the solution is concentrated under reduce pressure and the residue taken up with ethyl acetate. The organic solution is washed by:

a solution of sodium bicarbonate
a solution of sodium chloride
a solution of $KHSO_4/K_2SO_4$
a solution of sodium chloride The organic solution is dried over $MgSO_4$ and filtered. After 20 hours of rest, there is crystallization in each of the solutions. After filtration, the fractions coming from a crystallization in an aqueous medium are collected together and washed in water-saturated AcOEt to yield after filtration and drying in vacuo 7.78 g of product (m.p. 158°–159° C.).

The fraction coming from crystallization in AcOEt is washed in water-satured AcOEt to yield, after filtration and drying in vacuo, 6.18 g of product (m.p.: 150°–154° C.).

The aqueous phase and the organic phase give an additional crystallization. These latter two products are collected together and washed as before to yield 38.05 additional g of comparable quality.

Overall yield: 107.63 g—monitored by NMR and TLC

2. HCl, H-Gln-Gly-OMe

A solution of 61.8 g of Z-Gln-Gly-OMe (175.9 mM) in 704 ml of DMF, 880 ml of methanol and to which are added, with cooling by an ice bath, 176 ml of an N HCl solution, then 3.1 g of 10% Pd/C. After 3 hr. 30 mins. of hydrogenation under excess pressure of 35 cm of mercury, the catalyst is filtered over cellite and the solution is concentrated under reduced pressure. The residue is used directly in the following step.

3. Boc-Gln-Gln-Gly-OMe

A solution of the residue obtained in the preceding step (theoretically 175.9 mM) in 500 ml of DMF, cooled on an ice bath, has 77.6 g of Boc-Gln-ONp (211.1 mM), 26.4 g of hydroxy benzotriazole (211.1 mM) and N-ethylmorpholine added thereto until a pH of 7 is obtained. After 20 hrs. of reaction at ambient temperature, the solution sets en masse. By addition of ethyl acetate, a precipitate is obtained which is drained, washed with AcOEt and dried in vacuo. 64.27 g of product are obtained, viz. a yield of 82%.

Monitored by NMR and TLC.

4. TFA, H-Gln-Gln-Gly-OMe

A suspension cooled on an ice bath of 98.83 g of Boc-Gln-Gln-Gly-OMe (221.8 mM) in 300 ml of dichloromethane has 400 ml of TFA added thereto. After 30 mins. of reaction on an ice bath and one hour at ambient temperature, the solution is concentrated under reduced pressure up to half its initial volume and the residue is poured over stirred ether. After filtration, washing and drying in vacuo, 119 g of product are obtained.

5. Boc-Arg($NO_2$)-Gln-Gln-Gly-OMe

A solution of the 119 g of the preceding product in 1190 ml of DMF cooled on an ice bath has 77.91 g of Boc-Arg($NO_2$)-OH (244 mM), 97.51 g of BOP (266.2 mM) and N-ethylmorpholine added thereto until pH 7 is obtained. After 20 hrs. reaction at ambient temperature, the solution is poured over 8 liters of ethyl acetate. The precipitate obtained is filtered, washed with AcOEt then dried in vacuo. 153.7 g of product are obtained. Monitored by NMR and TLC.

6. TFA, H-Arg($NO_2$)-Gln-Gln-Gly-OMe

A suspension cooled on an ice bath of 153.7 g of Boc-Arg($NO_2$)-Gln-Gln-Gly-OMe (theoretically 221.8 mM) in 600 ml of dichloromethane has 750 ml of TFA added thereto. After one hour at ambient temperature, 250 ml of TFA are further added and 30 mins. later, 250 ml of TFA are added. After a further hour of reaction, the solution is concentrated to one third of the initial volume and the residue is poured over 3 liters of ether with stirring. The precipitate formed is drained, washed with ether and dried in vacuo. 167 g of product are obtained.

7. Boc-Ser-Arg($NO_2$)-Gln-Gln-Gly-OMe

A solution cooled on an ice bath of 167 g of TFA, H-Arg($NO_2$)-Gln-Gln-Gly-OMe (theoretically 221.8 mM) in 1.5 liters of DMF has added thereto 97.52 g of Boc-Ser-ONb (266.2 mM), 33.31 g of hydroxybenzotriazole (266.2 mM) and N ethylmorpholine until a pH of 7 is obtained. After 3 hrs. of reaction, at ambient temperature, part of the DMF is evaporated and the residual solution is poured over ethyl acetate with stirring. The precipitate is filtered, washed with ethyl acetate and dried in vacuo. 153.3 g of product are obtained, viz. a yield of 94.2% over 4 steps. Monitored by NMR and TLC.

8. Boc-Ser-Arg-Gln-Gln-Gly-OMe, AcOH

A solution of 153.3 g of Boc-Ser-Arg($NO_2$)-Gln-Gln-Gly-OMe (208.9 mM) in one liter of methanol, one liter of water and 500 ml of acetic acid is hydrogenated for 20 hours in the presence of 10 g of 10% Pd/C. After filtration of the catalyst and concentration of the solution, the residue taken up in water is lyophilized. 153 g of product are obtained, viz. a yield of 97.8%.

9. Boc-Ser-Arg-Gln-Gln-Gly-OH, HCl

A solution of 104.4 g of Boc-Ser-Arg-Gln-Gln-Gly-OMe (134.4 mM) in 2 liters of DMF has one liter of water, then 27.88 g of NaOH (697 mM) in 50 ml of water added thereto, with cooling by an ice bath. After 15 mins. of reaction at temperature close to 15° C., the product is neutralized by an N hydrochloric acid solution until a pH of 6.5 is obtained. After evaporation, the residue is triturated in ethyl acetate. The precipitate formed is drained, washed with AcOEt and dried in vacuo, then with air. 132.7 g of product are obtained.

Purification: 109 g of Boc-Ser-Arg-Gln-Gln-Gly-OH, HCl are purified by counter-current distribution in the n-butanol-methanol-water (4-1-5) mixture. After 700 transfers, the product is fractioned into three parts which, after evaporation and lyophilization, give: one fraction of 27.5 g and two fractions of 23.79 g and 16.90 g to be repurified.

Monitored by NMR and TLC-AAA: Ser: 0.91-Arg: =0.97-Gln(Glu): 2.05-Gly: 1.01

EXAMPLE V

Synthesis of Boc-Asp(OBzl)-Ile-Met-NH-NH$_2$ (fragment D)

1. Boc-Met-NH-NH Troc 4.31 g (10 mM) of Boc-Met-OH, DCHa in solution in 50 ml of ethyl acetate are treated in the presence of 20 ml of water by a saturated solution of potassium bisulfate up to pH=3, the aqueous phase is extracted several times with ethyl acetate and the extracts dried over magnesium sulfate. To this solution are added 2.28 g (11 mM) of H$_2$N-NH-Troc (Troc=2,2,2-trichloro ethoxycarbonyl, this reagent being prepared in accordance with YAJIMA, Chem. Pharm. Bull. 1971, 19, 420).

After cooling in an ice bath, 2.37 g (11 mM) of 97% DCC in solution in 10 ml of ethyl acetate are added. After one night during which the product returns progressively to ambient temperature, the dicyclohexylurea is filtered and dried (2.04 g) and the organic solution is washed successively with the following aqueous solutions:

5% sulfate-bisulfate twice ClNa 2M 2X 5% sodium bicarbonate twice, ClNa 3M twice and finally with water twice. After drying over magnesium sulfate and concentration of the solvent to virtual dryness, hexane is added until cloudiness begins and the product is kept at +4° C. overnight after which the precipitate formed is filtered, washed with a (4/1) mixture of hexane and ethyl acetate and dried in vacuo; 3.46 g (79%) are thus obtained: m.p.=92°-4° alpha D 25°=−32°-C=1, dioxane.

TLC in chloroform-methanol-AcOH 95/5/3—Rf=0.45

2. TFA, H-Met-NH-NH Troc 43.9 g (0.1M) of Boc-Met-NH-NH-Troc in solution in 200 ml of dichloromethane and 20 ml of ethane dithiol are treated with an ice bath in a nitrogen atmosphere and with stirring by 200 ml of trifluoroacetic acid, the cold bath is removed and the product is left with stirring for one hour. The product is isolated by elimination of the volatile reagents firstly under 20 mm then 0.1 mm of pressure, the residual oil is taken up twice with 75 ml of isopropanol by evaporating in vacuo then washed twice by 75 ml of hexane by decantation after which it is dried in vacuo in the presence of potassium hydroxide overnight, after which it begins to solidify and is used as such in the following operation.

3. Boc-Ile-Met-NH-NH-Troc

The above oil (about 0.1M) of TFA, H-Met-NH-NH Troc in solution in 6500 ml of ethyl acetate and cooled in an ice bath is treated with 12.7 ml (0.1M) of N ethyl morpholine then 14.85 g (0.1M) of HOBt, 1H$_2$O then by 34.35 g (0.08M) of Boc-Ile-OSu followed by 12.7 ml (0.1M) of N ethylmorpholine (NEM). After ½ hour, the cold bath is removed and subsequently NEM is added periodically so as to maintain the apparent pH towards 7.

After 20 hrs., the reaction is complete and isolation is effected by successive washings with the following aqueous solutions: 5% sulfate-potassium bisulfate 3 times, water: three times, 5% sodium bicarbonate: 3 times and finally, water, up to neutrality.

After drying over magnesium sulfate and evaporation of the solvent in vacuo, 64 g of gum are obtained, chromatographed over a column of silica with dichloromethane containing from 0 to 1.5% of methanol. 30 g (68%) of product having an HPLC purity of 98.9% and an NMR spectrum in accordance with the expected structure, are thus obtained, m.p.: 88°-92°.

4. TFA, H-Ile-Met-NH-NH-Troc 27.6 g (50 mM) of Boc-Ile-Met-NH-NH-Troc in solution in 140 ml of dichloromethane and 14 ml of ethane dithiol are cooled with an ice bath and stirred in an atmosphere of nitrogen then 140 ml of trifluoroacetic acid are added thereto in 5-6 mins. The cold bath is removed and, after 45 mins., the product is isolated by evaporation of the reagents to a maximum, take-up of the residual oil by 2×60 ml of isopropanol followed by evaporation and finally by 2 washings with 60 ml of pentane. After drying for one night over potassium hydroxide in vacuo, an oil of vitreous appearance is obtained which is used in the following operation (30 g).

5. Boc-Asp(OBzl)-Ile-Met-NH-NH-Troc

The preceding 30 g of oil in solution in 250 ml of THF are treated with 6.4 ml (50 mM) of NEM and 18.9 (45 mM) of Boc-Asp(OBzl)O Su. The apparent pH is adjusted between 6 and 7 by successive additions of NEM. After 4 hours, the product is isolated by evaporation of the THF, take-up in 400 ml of ethyl acetate followed by the same washings as the preceding homologue (3). The residue after drying and evaporation (36.5 g) is purified by chromatography over a column of silica with dichloromethane as solvent containing from 0 to 1.5% of methanol. 25 g (66%) of product presenting an NMR spectrum in accordance with the expected structure are thus obtained.

m.p.=96°-100°.

6. Boc-Asp(OBzl)-Ile-Met-NH-NH$_2$ 7.57 g (10 mM of Boc-Asp(OBzl)-Ile-Met-NH-NH-Troc in solution in 80 ml of the 80/20 mixture of DMF-AcOH are treated at ambient temperature with 6.54 g of zinc in fine powder form with stirring for 30 mins. The product is isolated by filtration of the zinc, treatment of the filtrate by 800 g of ice, then filtration after melting of the ice followed by repeated washings with water. The white solid is firsly dried in air then in a high vacuum in the presence of potassium hydroxide and phosphoric anhydride. 5.60 g (96%) of product with about 95% purity according to TLC and NMR are thus ob-

EXAMPLE VI

Boc-Arg-Lys(Z)-Leu-Leu-OH (fragment $E_1$)

1. Boc-Leu-Leu-OMe

In 500 ml of dioxane containing 18.4 g of NEM (0.16M), 9.05 g of H Leu OMe, HCl (0.05M), 7.4 g of HOBt (0.055M) and 18 g of Boc-Leu-ONSu (0.055M) are added successively. The product is stirred at ambient temperature for 18 hours and the pH is adjusted to 6–7 by NEM, with pH paper, if necessary in the course of reaction. The solvent is evaporated, the residue is dissolved in AcOEt and the organic solution is successively washed twice with 5% $KHSO_4$-$K_2SO_4$, ClNa/water, 5% $NaHCO_3$, ClNa/water. The product is dried over $MgSO_4$ and the solvent is evaporated. The residue is dissolved in the minumum of ether and the product is precipitated by pentane, drained, dried.

Yield: 15 g (83%), TLC: chloroform-methanol-acetic acid, 95-5-3.

AcOEt-hexane 25/75—m.p.: 131–136
Possibility of purification over silica gel 60 Merck (70–230 mesh) in chloroform, with elution by the same solvent

2. H-Leu-Leu-OMe, TFA 27.5 g of Boc-Leu-Leu-OMe (0.076M) are covered with 180 ml of TFA at ambient temperature: a slight heating occurs. After 30 mins. the solvent is evaporated, the residual oil is taken up in ether and the product is scratched: a white precipitate is formed; pentane is added, the product is drained, dried.

Yield: 28.2 g (100%), TLC: chloroform-methanol-acetic acid 95/5/3, chloroform-methanol-acetic acid 80/15/5.

3. Boc-Lys(Z)-Leu-Leu-OMe

In 600 ml of AcOEt cooled with an ice bath, the following are successively added:
28.2 g of H-Leu-Leu-OMe, TFA (0.076M)
26.22 g of NEM (0.0228M)
11.23 g of HOBt (0.083M)
46.4 g of Boc-Lys(Z)OTcp (0.083M).

The product is stirred, then the cold bath is removed. The pH is adjusted to 6–7 by NEM if necessary. After 18 hours, the organic solution is successively washed with 5% $KHSO_4$-$K_2SO_4$, ClNa/water, 5% $NaHCO_3$, ClNa/water. The product is dried over $MgSO_4$. The solvent is evaporated, the residual oil is dissolved in chloroform and deposited at the top of a column (L: 90 cm—diam. 5 cm) of silica gel 60 Merck (70–230 mesh) in chloroform. The product is eluted with chloroform, fractionated. The fractions containing the pure product are evaporated, the foam obtained is redissolved in ether and evaporated to dryness. The residue is triturated in pentane, drained and dried.

Yield: 42.4 g (91%), TLC: AcOEt/hexane ½, chloroform-MeOH-AcOH 95/5/3, Monitored by NMR-HPLC-EPP: 98.7%.

4. Boc-Arg-Lys(Z)-Leu-Leu-OMe 15.5 g of Boc-Lys(Z)-Leu-Leu-OMe (0.025M) are covered with 100 ml of TFA at ambient temperature. After 30 mins. with occasional stirring, the solvent is evaporated completely. The residual oil is dissolved in 150 ml of dioxane and the pH is brought to 6–7 by DIPEA, with pH paper. The product is cooled with an ice bath and 7.21 g of Boc-Arg-OH, $H_2O$, HCl (0.025M), 13.44 g of BOP (0.03M) and 10.32 g of DIPEA (0.08M) are added. The product is stirred, then the cold bath is removed and the pH is adjusted to 6–7 by DIPEA if necessary. After 18 hours, the dioxane is evaporated, the residual oil is dissolved in AcOEt and washed successively with 5% $NaHCO_3$, ClNa/water. The product is dried over $MgSO_4$, the solvent is evaporated and the oil is dissolved in 5-95 MeOH-chloroform, saturated with water, then deposited at the top of a column (L: 85 cm—diam. 4 cm) of silica gel 60 Merck (70–230 mesh) in the same mixture. The product is eluted with:

1.5 l of MeOH-chloroform 5-95 saturated with water
1.1 of MeOH-chloroform 7.5-92.5 saturated with water
2.5 l of MeOH-chloroform The product is fractionated and the pure fractions are evaporated, taken up in ether, evaporated and extracted completely in vacuo.

Yield: 16.8 g (87%), TLC: chloroform-MeOH-AcOH 95-5-3, chloroform-MeOH-AcOH 80-15-5, Monitored by NMR-HPLC-EPP 91.8%.

5. Boc-Arg-Lys(Z)-Leu-Leu-OH 13.98 g of Boc-Arg-Lys(Z)-Leu-Leu-OMe (0.018M) are solubilized in 250 ml of MeOH; 40 ml of water are added, then, at ambient temperature, 5.67 g of baryta (0.018M), finely pulverized. The product is stirred for 2 hrs. 30 at ambient temperature. The end of reaction is monitored by TLC. $CO_2$ is bubbled in up to pH 6, the product is filtered. The filtrate is evaporated, the residue is solubilized in isopropylic alcohol and filtered, the alcohol is concentrated and the product is precipitated by ether.

Yield: 12.31 (89%), TLC: chloroform-MeOH-AcOH 90/15/5, 2-butanol-AcOH-water 72/7/21, Monitored by NMR-HPLC-EPP 95.88.

EXAMPLE VII

Boc-Gln-Leu-Ser-Ala-OMe (fragment $F_1$)

1. Boc-Ser-Ala-Ome 25 g of H-Ala-OMe, HCl and 66 g. of Boc-Ser-ONb are dissolved in 500 ml DMF. The product is cooled in an ice bath and 25 ml of NEM, 24 g of N-hydroxy benzotriazole are added with magnetic stirring and the pH is maintained at 6.5 or 7 by addition of NEM. The product is stirred for 18 hrs. at ambient temperature. After TLC monitoring, the medium is evaporated to 90% (0.1 mm Hg—35° C.). The oil obtained is dissolved in 1.500 ml of chloroform, the product is washed with a solution of saturated sodium chloride (twice), 5% sulfate/potassium bisulfate solution (3 times), saturated sodium bicarbonate (5 times). The solution is dried over $Na_2SO_4$ and evaporated to dryness. An oil is obtained which is dried to constant weight (30°—0.1 mm Hg).

Yield: 53.78 g—Monitored by TLC.

2. H-Ser-Ala OMe, TFA 52.8 g of Boc-Ser-Ala-OMe are dissolved in 100 ml of methylene chloride with magnetic stirring, being cooled with an ice bath. 250 ml of cooled TFA are added and the product is stirred for 20 mins. at ambient temperature and filtered. The filtrate is evaporated to dryness (35° water-jet pump). By addition of 2 l of ether, a white solid precipitates. It is drained, washed with ether (3 times), dried to constant weight (30°—0.1 mm Hg).

Yield: 40.82 g.

3. Boc-Leu-Ser-Ala-OMe 40 g of H-Ser-Ala-OMe, TFA and 32.9 g of Boc-Leu-OH, H$_2$O are dissolved in 400 ml of DMF. The product is cooled with an ice bath with magnetic stirring and 14.4 ml of NEM then 65.8 g of BOP and enough NEM to maintain the pH at 6.5-7 are added. The product is stirred for 2 hrs. at ambient temperature. After monitoring by TLC, the product is evaporated to dryness (0.1 mm—35°) and the oil obtained is dissolved in 1500 ml of chloroform, washed twice with a saturated NaCl solution, three times with 5% sulfate/potassium bisulfate, 3 times with saturated sodium bicarbonate, dried over Na$_2$SO$_4$, evaporated to dryness (30°—water-jet pump). The oil obtained is solidified in ether: Fraction A=29 g. A second jet B is obtained by addition of hexane, identical in TLC: B=13.7 g.

Yield: 42.7 g. Monitored by NMR and TLC.

4. H-Leu-Ser-Ala-OMe, TFA 29 g of Boc-Leu-Ser-Ala-OMe are suspended in 50 ml of methylene chloride with magnetic stirring, being cooled by an ice bath. 100 ml of cooled TFA are added and, after dissolution, the product is stirred for 30 mins. at ambient temperature and filtered. The filtrate is evaporated to dryness (35°—water-jet pump). The oil obtained is solidified in ether (the solvent is changed several times). The product is dried to constant weight (30°—0.1 mm Hg)

Yield: 30.2 g.

5. Boc-Gln-Leu-Ser-Ala-OMe 30 g of H-Leu-Ser-Ala-OMe, TFA and 25.5 g of Boc-Gln-ONp are dissolved, with magnetic stirring, in 300 ml of DMF. The product is neutralized with 9.7 ml of NEM. 10 g of OHBt are added and the product is stirred for 2 hours at ambient temperature, maintaining the pH at 6.5-7 by addition of NEM.

After monitoring by TLC, the medium is concentrated to 90% (0.1 mm Hg—35°), taken up in 1000 ml of chloroform: a product precipitates into gel. The product is drained, washed, being taken up in 500 ml of chloroform (twice) then in ether (3 times). The product is dried to constant weight (0.1 mm Hg—30°).

Yield: 32.1 g, TLC: chloroform/MeOH/AcOH: 9/2/0.5—Rf=0.81 HPLC: EPP=91% AAA: Ser: 0.86-Glu: 1.02-Ala: 0.99-Leu: 0.99.

EXAMPLE VIII

Boc-Tyr-Arg-Lys(Z)-Val-Leu-Gly-OH, HCl (fragment G$_1$)

1. Z-Leu-Gly-OCH$_3$ 0.22 mole of Z-Leu-OH are dissolved in 500 ml of DMF. To this solution are successively added:
25.11 g of HCl H-Gly-OCH$_3$ (0.2 mole)
28 ml of NEM
96 g of BOP (0.22 mole)
then the pH is adjusted to 7 by addition of NEM.

The reaction mixture is stirred at ambient temperature, maintaining the pH at 7 by addition of NEM if necessary. The reaction is followed in TLC (chloroform-methanol-acetic acid 95-5-9). After 2 hours, the reaction is completed. The reaction mixture is evaporated to dryness under reduced pressure (0.2 mm of mercury) and at a temperature lower than 30° C. The residue is taken up in ethyl acetate (1 liter).

The solution is washed successively with:
aqueous solution of bicarbonate (4×200 ml)
aqueous solution of SO$_4$HK-SO$_4$K$_2$ (4×200 ml)
saturated aqueous solution of sodium chloride (2×200 ml)
dried over magnesium sulfate and evaporated to dryness under reduced pressure. The residue is taken up in ether (500 ml), triturated, drained, dried.

Yield: 56.7 g (84.28%), TLC: chloroform-methanol-acetic acid 95-5-3 Rf: 0.44.

2. HCl-H-Leu-Gly-OCH$_3$ 56 g (0.166 mole) of Z-Leu-Gly-OCH$_3$ are dissolved in 900 ml of 0.23N hydrochloric methanol. To this solution are added 6 g of 10% Pd/C containing 50% humidity. Hydrogenation is carried out for 24 hours at ambient temperature and under atmospheric pressure. The catalyst is filtered and the solution is evaporated to dryness under reduced pressure at a temperature lower than 30° C. The residue is taken up in ether (2×50 ml),. is decanted and the product is dried in a desiccator in the presence of phosphoric anhydride. A white powder is obtained.

Yield: 33.53 g (84.4%), TLC: chloroform-methanol-acetic acid 90-20-9 Rf: 0.15, Monitored by NMR.

3. Boc-Val-Leu-Gly-OCH$_3$ 28.24 g of Boc-Val-OH (0.13 mole) are dissolved in 400 ml of tetrahydrofuran cooled to −10° C. 14.45 ml (0.13 mole) of isobutyl chloroformate are then added. The mixture is stirred strongly at −10° C. for 15 minutes. To this mixture is added a solution of tetrahydrofuran cooled to −10° C. containing 31.5 g of HCl H-Leu-Gly-OCH$_3$ (0.13 mole) previously neutralized by 14.45 ml of N methylmorpholine. Stirring is continued whilst cooling the reaction mixture in an ice bath (2 hours) then at ambient temperature for 2 hours. The reaction mixture is evaporated to dryness under reduced pressure at a temperature lower than 30° C. The residue is taken up in a 500 ml-500 ml mixture of ethyl acetate-water. The aqueous phase is decanted and the organic phase washed successively with
an aqueous solution of sodium bicarbonate (2×50 ml)
an aqueous solution of SO$_4$HK-SO$_4$K$_2$ (pH 2) (2×50 ml)
an aqueous solution of sodium chloride (50 ml)
then dried over magnesium sulfate and evaporated to dryness under reduced pressure at a temperature lower than 30° C. The residue is taken up with pentane (50 ml), drained and dried in vacuo (0.1 mm of mercury).

Yield: 39.7 g (76%); TLC: chloroform-acetone 75-25 Rf: 0.46, Monitored by NMR.

4. TFA H-Val-Leu-Gly-OCH$_3$ 39 g of Boc-Val-Leu-Gly-OCH$_3$ (0.097 mole) are dissolved in 190 ml of TFA cooled in an ice bath. After dissolution, the ice bath is removed and the mixture is stirred for 30 mins. at ambient temperature. The product is evaporated to dryness under reduced pressure and the residue is taken up in ether (100 ml), triturated and the ether is decanted. This operation is repeated twice and the last traces of solvents are eliminated under reduced pressure (0.1 mm of mercury).

Yield: 44.8 g, TLC: chloroform-methanol-acetic acid 90-20-3 Rf: 0.36.

5. Boc-Lys(Z)-Val-Leu-Gly-OCH$_3$ 25.55 g of TFA H-Val-Leu-Gly-OCH$_3$ (0.0615 mole) are dissolved in 200 ml of DMF. The solution is taken to pH 7 by addition of NEM. There are then added to this solution 32.47 g of Boc-Lys(Z)-OTCP (0.058 mole) and 9 g of HOBT (0.059 mole). The pH of the reaction mixture is returned to 7 by addition of NEM. The product is stirred at ambient temperature, maintaining the pH at 7 by addition of NEM if necessary. The reaction is followed in TLC: chloroform-methanol, 90-10; chloroform-methanol-acetic acid, 90-20-3 (2 media).

After one hour, 1.96 g of Boc-Lys(Z)-OTCP (0.0035 mole) and 0.61 g of HOBT are added. The pH of the solution is returned to 7 by addition of NEM.

Two hours afterwards, the reaction is completed in TLC. The reaction mixture is then evaporated to dryness under reduced pressure (0.1 mm of mercury) at a temperature lower than 30° C. The residue is taken up with 500 ml of water, triturated. The solid formed is drained then washed with 500 ml of aqueous solution of HKSO$_4$-K$_2$SO$_4$ (pH 2)
500 ml of a saturated aqueous solution of sodium bicarbonate
200 ml of water then with ether (200 ml×2) and dried.

The impure product is chromatographed over a column of silica gel (5 cm×150 cm). It is eluted with the 80-20 mixture of chloroform-ethyl acetate (rate 600 ml/hr.)

The good fractions determined in TLC are collected together, evaporated to dryness under reduced pressure. The residue is taken up in ether, triturated and the solid obtained drained. White powder, 35.14 g (86%).

TLC: chloroform-methanol 90-10 Rf: 0.62, chloroform-methanol-acetic acid, 87.7-9.4-2.8 Rf: 0.52, Monitored by NMR, AAA: AC Gly 1.00-Val 0.96-Leu 1.06-Lys 0.98.

6. TFA H-Lys(Z)-Val-Leu-Gly-OCH$_3$ 15 g of Boc-Lys(Z)-Val-Leu-Gly-OCH$_3$ (22.6 mM) are dissolved in a mixture of TFA-methylene chloride (75 ml/75 ml). The product is stirred for 40 mins. at ambient temperature, then evaporated to dryness under reduced pressure at a temperature lower than 30° C. The residue is taken up in ether containing 20% of hexane (100 ml). The solid formed is drained and dried. A white solid of 14.51 g is obtained. Yield: 94.7%, TLC: chloroform/methanol/acetic acid (95/5/3) Rf: 0.12.

7. Boc-Arg(HCl)-Lys(Z)-Val-Leu-Gly-OCH$_3$ 14.1 g of TFA H-Lys(Z)-Val-Leu-Gly-OCH$_3$ (21 mM) are dissolved in 50 ml of DMF. The solution is taken to pH 6-7 by addition of NEM. 6.57 g of Boc-Arg(HCl)-OH.1 H$_2$O (20 mM) and 10.6 g of BOP (24 mM) are then added to this solution. The pH of the reaction medium is returned to 6-7 by addition of NEM. The product is stirred at ambient temperature, maintaining the pH at 6-7 by addition of NEM if necessary. The reaction is followed in TLC: chloroform/methanol (80/20).

After 5 hrs., the reaction is completed. The reaction mixture is evaporated to dryness under reduced pressure (0.1 mm of mercury) and at a temperature lower than 30° C. The oil obtained is taken up in 300 ml of ethyl acetate. The solid formed is drained and washed with ether (1st jet). Ether is added to the preceding filtrate; a solid precipitates which is drained (2nd jet): The two jets are identical in TLC. They are washed in the solid state by stirring for 1 hour with a mixture of 200 ml of ethyl acetate saturated water and 60 ml of water. The solid is drained, then washed with 60 ml of water and 300 ml of ether and dried.

Yield: 78.7% (13.49 g), TLC: chloroform/methanol (20/20)—Rf=0.32, Monitored by NMR.

8. TFA H-Arg(HCl)-Lys(Z)-Val-Leu-Gly-OCH$_3$ 13.3 g of Boc-Arg(HCl)-Lys(Z)-Val-Leu-Gly-OCH$_3$ (15.5 mM) are dissolved in a (60 ml/60 ml) mixture of TFA-methylene chloride. The product is stirred for 40 mins. at ambient temperature then evaporated to dryness under reduced pressure at a temperature lower than 30° C. The residue is taken up by a (80/20:100 ml) mixture of ether-hexane. The solid formed is drained, washed with hexane and dried (weight: 15.13 g).

TLC: chloroform/methanol (3/1)—Rf: 0.35

9. Boc-Tyr-Arg(HCl)-Lys(Z)-Val-Leu-Gly-OCH$_3$ 15.5 mM of TFA H-Arg(HCl)-Lys(Z)-Val-Leu-Gly-OCH$_3$ are dissolved in 50 ml of DMF. The solution is taken to pH 6 by addition of NEM. 8.20 g of Boc-Tyr-OTCP (15.5×10 mM) and 2.41 g of HOBT (15.5×10 mM) are then added to this solution. The pH is returned to 6 by addition of NEM. The reaction mixture is stirred at ambient temperature, maintaining the pH at 6 by addition of NEM if necessary. The reaction is followed in TLC: chloroform/methanol (3/1). After 3 hrs., the reaction is terminated. The reaction mixture is evaporated to dryness under reduced pressure (0.1 mm of mercury) and at a temperature lower than 30° C. The residual oil is taken up in ethyl acetate (300 ml). The gelatinous solid formed is drained, washed with ethyl acetate (100 ml), with ethyl acetate-ether (1/1:100 ml) then with ether (100 ml), finally with hexane (100 ml). The product is dried under reduced pressure up to constant weight. Yield: 96% (15.14 g).

TLC: chloroform/methanol (3/1)—Rf: 0.47—Monitored by NMR, AAA: AC: Gly: 0.95-Val: 0.98-Leu: 1.02-Lys: 1.01-Arg: 1.01—Tyr: 1.05, HPLC: 93.81% EPP.

10. Boc-Tyr-Arg(HCl)-Lys(Z)-Val-Leu-Gly-OH 7 g of Boc-Tyr-Arg(HCl)-Lys(Z)-Val-Leu-Gly-OCH$_3$ (6.86 mM) are dissolved in a mixture of 70 ml of dioxane and 35 ml of water. 6.4 ml of 4N sodium hydroxide (25.6 mM): 3.7 equiv.) are added to this solution and the product is stirred for 30 mins. at ambient temperature. It is diluted with 200 ml of water and 800 ml of ethyl acetate. The mixture is then acidified to pH 3 by addition of (N) HCl. The ethyl acetate is decanted and the solid is drained (1st jet). The ethyl acetate is evaporated to dryness; a 2nd jet is obtained. The two jets, identical in TLC, are collected together, washed with ether and dried.

Yield: 74.7% (5.16 g), TLC: chloroform/methanol (2/1)—Rf: 0.45, 1H monitoring by NMR, AAA: Ac: Gly: 1.00-Val: 0.97-Leu: 1.04-Tyr: 0.95-Lys: 0.99-Arg: 1.05 HPLC-EPP 91.52%.

EXAMPLE IX

Boc-Ile-Phe-Thr-Asn-Ser-NH-NH$_2$ (fragment H$_1$)

1. Boc-Asn-Ser-OMe

A solution of 23.32 g of Boc-Asn-OH (0.1M) and 19.7 g of NbOH (0.11M) in 250 ml of DMF, cooled on an ice bath, has 22.69 g of DCCI added thereto. After 3 hrs. reaction at ambient temperature, the DCU is filtered, cooled on an ice bath and 15.56 g of HCl, H-Ser-OMe are added. The pH is taken to, then maintained at 7 by addition of NEM. After 4 hrs. at ambient temperature and 20 hrs. at +4° C., the solution is concentrated under reduced pressure. The residue is taken up in the (50/50) mixture of AcOEt/n-butanol. The organic solution is washed successively with:
- a saturated solution of sodium bicarbonate
- a saturated solution of sodium chloride
- a solution of 5% KHSO₄/K₂SO₄
- a saturated solution of sodium chloride.

After drying over MgSO₄ and evaporation under reduced pressure, the residue is crystallized in the ether-hexane mixture. The product is filtered, washed with ether/hexane and dried in vacuo yielding 26.9 g of product.

Yield: 80.8%—Monitored by NMR and TLC

2. TFA, H-Asn-Ser-OMe

A solution cooled on an ice bath of 13.5 g of Boc-Asn-Ser-OMe (40.5 mM) in 54 ml of dichloromethane has 81 ml of TFA added thereto. After one hour of reaction at ambient temperature, the solution is concentrated under reduced pressure, the residue is taken up with ether. A thick oil is obtained which is used in the following reaction.

3. Boc-Thr-Asn-Ser-OMe

A solution cooled on an ice bath of the crude product previously obtained in 300 ml of DMF has 14.09 g of Boc-Thr-ONSu (44.44 mM), 5.58 g of HOBt (41.3 mM) and NEM added thereto until a pH of 7 is obtained. After 20 hrs. of reaction at ambient temperature, the solution is concentrated under reduced pressure and the residue is taken up in the AcOEt/n butanol mixture. The organic solution is successively washed with:
- a saturated solution of sodium bicarbonate
- a saturated solution of sodium chloride
- a solution of 5% KHSO₄/K₂SO₄
- a saturated solution of sodium chloride.

After drying over MgSO₄, the solution is concentrated under reduced pressure and the residue crystallized in the ether/hexane mixture. 8.28 g of product are obtained.

Yield: 47%—Monitored by NMR and TLC

4. TFA, H-Thr-Asn-Ser-OMe

A solution cooled on an ice bath of 8 g of Boc-Thr-Asn-Ser-OMe in 32 ml of dichloromethane has 54 ml of TFA added thereo. After one hour of reaction at ambient temperature, the solution is concentrated under reduced pressure and the residue precipitated with ether. After filtration, it is used as such in the following reaction.

5. Boc-Phe-Thr-Asn-Ser-OMe

A solution of the precipitate obtained in the preceding step in 100 ml of DMF has 7.82 g of Boc-Phe-ONp (20.24 mM), 2.53 g of HOBt (18.71 mM) and N-ethyl morpholine added thereto, with cooling by an ice bath, until a pH of 7 is obtained. After 4 hrs., the solution is concentrated under reduced pressure and the residue is taken up in AcOEt. The organic solution is washed with:
- a saturated solution of sodium bicarbonate
- a saturated solution of sodium chloride
- a solution of 5% KHSO₄/K₂SO₄
- a saturated solution of sodium chloride After drying over MgSO₄, concentration of the organic phase, the residue is crystallized in ether. 10 g of product are obtained.

Yield: 93.5% Monitored by TLC and NMR.

6. TFA, H-Phe-Thr-Asn-Ser-OMe

A solution of 10 g of Boc-Phe-Thr-Asn-Ser-OMe (17.19 mM) in 40 ml of dichloromethane has 60 ml of TFA added thereto, with cooling by an ice bath. After one hour of reaction at ambient temperature, the product is precipitated with ether. The gum obtained after drying yields 5.14 g of product.

Yield: 48.5%.

7. Boc-Ile-Phe-Thr-Asn-Ser-OMe

A solution cooled on an ice bath of 5.14 g of TFA, H-Phe-Thr-Asn-Ser-Ome (8.78 mM) in 100 ml of DMF has 3.17 g of Boc-Ile-OSu (9.66 mM), 1.30 g of HOBt (9.62 mM) and N-ethyl morpholine added thereto until a pH of 7 is obtained. After 20 hours of reaction at ambient temperature, the solution is concentrated under reduced pressure and the residue taken up in ether gives a precipitate which is filtered and dried in vacuo. 5.24 g of product are obtained.

Yield: 85.9%—Monitored by NMR and HPLC.

8. Boc-Ile-Phe-Thr-Asn-Ser-NH-NH₂

A solution of 5 g of Boc-Ile-Phe-Thr-Asn-Ser-OMe (7.2 mM) in 40 ml of DMF and 200 ml of methanol cooled on an ice bath has 3.6 ml of an 80% solution of hydrazine hydrate added thereto. After 21 hours of reaction at ambient temperature, 0.9 ml of the same solution of hydrazine hydrate are added. After 3 more hours, the gel obtained is filtered, washed with methanol and dried in vacuo. 3.94 g of product are obtained.

Yield: 78.8%—Monitored by NMR and TLC.

EXAMPLE X

Boc-Tyr-Ala-Asp(OBzl)-Ala-OH (fragment I)

1. Boc-Asp(OBzl)-Ala-OBut 3.62 g (0.02 mole) of hydrochloride of tertiobutyl alaninate are suspended in 30 ml of acetonitrile. 2.52 ml of NEM are added then 8.4 g (0.02 mole) of Boc-Asp(OBzl) ONsu. The pH is maintained at 6–6.5 by addition of NEM. Stirring is continued for 18 hours. After monitoring by TLC, the medium is evaporated to dryness, the oil is taken up in 50 ml of ACOET, the solution washed twice with a solution of KHSO₄/K-2SO₄, then with salted water, dried over Na₂SO₄ and evaporated to dryness. The oil obtained is dissolved in hexane, a little solid is filtered and the filtrate is evaporated to dryness. The oil obtained is used as such.

TLC: CHCl₃/acetone/ACOH 80/15/5—Rf=0.8.

2. Boc-Ala-Asp(OBzl)-Ala-OH

The crude oil obtained previously is dissolved in 50 ml of iced TFA and stirred for 1 hr. 30 mins. at ambient temperature. The TFA is evaporated to a maximum and the residual oil is taken up three times in anhydrous ether and decanted. It is then dried in a desiccator in vacuo in the presence of pentane. A solid foam is formed which is crushed and returned to be dried.

9.4 g of crude product is obtained, used as such for coupling.

The above TFA salt is dissolved in a mixture of 20 ml of DMF and 18 ml of distilled water. NEM is added up to a pH of 7 (using the pH-meter). 4 g (0.014 mole) of Boc-Ala-ONsu in solution in 16 ml of DMF are introduced. The pH is maintained at 6.5–7 by addition of NEM. After 5 hrs. 30 mins., the reaction is terminated (monitored by TLC). The solvent is evaporated to a maximum and the residue is taken up in a mixture of water and ethyl acetate. The organic phase is washed with a solution of $NaHCO_3$, with salted water, dried over $Na_2SO_4$ and evaporated to dryness. The residue is dissolved in ether and precipitated by hexane to give a gum which crystallizes after trituration.

The solid is drained and dried in air.

Yield: 5.05 g TLC: $CHCl_3$-acetone-ACOH 80-15-5—Rf=0.28.

3. Z-Tyr-Ala-Asp(OBzl)-Ala-OH 1 g (2 mmoles) of Boc-Ala-Asp(OBzl)-Ala-OH is introduced into 10 ml of stirred ice TFA.

After 30 mins. of stirring at ambient temperature, the TFA is evaporated to a maximum, the residue taken up twice in anhydrous ether and decanted, then dried in a desiccator in vacuo in the presence of potassium hydroxide. A solid foam is formed.

The crude product is dissolved in a mixture of 4 ml DMF and 2 ml of distilled water. NEM is added up to pH 7–7.5. 1 g (2.4 mmoles) of 1-Tyr-ONsu is then added and the pH is maintained at 7–7.5 by NEM (pH-meter). After 2 hrs. 30 mins., after monitoring by TLC, the solvent is evaporated to a maximum at 40° C. The residue is taken up in ethyl acetate and washed with water; a little solid is eliminated and the ethyl acetate is washed with the mixture of sulfate bisulfate and salted water. After the product has been left for a few hours, a precipitate is formed which is drained, washed with ether and dried in air.

500 mg are thus obtained. A 2nd jet of 350 mg, slightly less pure, is obtained by concentration of the ethyl acetate.

TLC chloroform-ACOH 3-1 Rf: 0.4, butanol-ACOH-$H_2O$ 72-7-2 Rf: 0.85, chloroform-acetone-ACOH 80-15-5 Rf: 0.1.

HPLC 90.9% polypeptide purity.

Monitored by NMR.

EXAMPLE XI

Synthesis of:
H-Arg-Lys(Z)-Leu-Leu-Gln-Asp(Bzl)-Ile-Met-Ser-Arg-Gln-Gln-Gly-Glu(OBzl)-Ser-Asn-Gln-Glu(OBzl)-Arg-Gly-Ala-Arg-Ala-Arg-Leu-$NH_2$ (peptide K)

1. Boc-Glu(OBzl)-Arg-Gly-Ala-Arg-Ala-Arg-Leu-$NH_2$, 3 HCl 34.47 g of H-Ala-Arg-Ala-Arg-Leu-$NH_2$, 3 HCl (57 mM) are dissolved in 230 ml of DMF. 28 g of BOP (63 mM) are added, then in one hour 33.5 g (57 mM) of Boc-Glu(OBzl)-Arg-Gly-OH in solution in 190 ml of DMF. The pH of the reaction medium is maintained at around 6 by addition of NEM. After 4 hours, the reaction medium is concentrated in vacuo by half and the residue poured over 800 ml of ethyl acetate. The precipitate obtained is filtered, washed with ethyl acetate, with ether and dried in vacuo. 56.8 g of product are obtained with a yield of 80%.

Identification: 1H NMR and AAA: Glu: 0.98-Gly: 1.01-Ala: 1.97-Leu: 1.05-Arg: 2.97.

HPLC reverse phase EPP 95%—TLC in EPAW 40/20/10/6—Rf=0.55.

2. H-Glu(OBzl)-Arg-Gly-Ala-Arg-Ala-Arg-Leu-$NH_2$, TFA, HCl 55.3 g of the above product are stirred for 30 mins. in 250 ml of $CH_2Cl_2$+250 ml of TFA. Then the reaction medium is concentrated in vacuo by half and poured over 1200 ml of iced ether. The precipitate obtained is filtered, washed with ether, dried in vacuo over potassium hydroxide. Yield: 100%.

3. Boc-Glu(OBzl)-Ser-Asn-Gln-Glu(OBzl)-Arg-Gly-Ala-Arg-Ala-Arg-Leu-$NH_2$, HCl

To the preceding TFA salt (45 mM) dissolved in 400 ml of DMF and neutralized by NEM, are added 22.2 g of BOP (50 mM) then, in one hour, 30 g (45 mM) of Boc-Glu(OBzl)-Ser-Asn-Gln-OH in solution in 300 ml of DMF. The pH of the reaction medium is maintained at 6. After 6 hours, the medium is concentrated by half in vacuo at 30° C. then poured over 1200 ml of ethyl acetate. The precipitate formed is filtered, washed with ethyl acetate, then with ether and finally dried in vacuo. Yield: 60.5 g (75%).

Product identified by NMR and AAA: Asp: 1.00-Ser: 0.81-Glu: 2.71-Gly: 0.89-Ala: 1.82-Leu: 0.96-Arg: 3.02-HPLC reverse phase EPP 70%—TLC: EPAW 30/20/10/6: Rf: 0.35.

4. H-Glu(OBzl)-Ser-Asn-Gln-Glu(OBzl)-Arg-Gly-Ala-Arg-Ala-Arg-Leu-$NH_2$, TFA, HCl 53.3 g (30 mM) of the above product are stirred for 35 mins. in 250 ml of dichloromethane plus 250 ml of TFA. After concentration in vacuo by half, the residue is poured over 1300 ml of iced ether; the precipitate formed is filtered, washed with ether, then dried in vacuo over potassium hydroxide.

5. Boc-Ser-Arg-Gln-Gln-Gly-Glu(OBzl)-Ser-Asn-Gln-Glu(OBzl)-Arg-Gly-Ala-Arg-Ala-Arg-Leu-$NH_2$, HCl

The preceding TFA salt is dissolved in 300 ml of DMF and neutralized by NEM. 14.8 g of BOP (33 mM) are added then, in small portions in one hour, 21.4 g (30 mM) of Boc-Ser-Arg-Gln-Gln-Gly-OH. The pH of the reaction medium is maintained at around 6 by NEM. After 7 hours, the medium is poured over 2 l of ACOEt. The precipitate obtained is filtered, washed with ethyl acetate, then with ether and finally dried in vacuo. Yield: 57 g (80%).

Product identified by NMR, AAA-Ser: 1.7-Arg: 4.1-Glu: 4.7-Gly: 2.05-Asp: 1.00-Ala: 1.91-Leu: 0.97-TLC BPEW1 Rf: 0.35.

6. H-Ser-Arg-Gln-Gln-Gly-Glu(OBzl)-Ser-Asn-Gln-Glu(OBzl)-Arg-Gly-Ala-Arg-Ala-Arg-Leu-$NH_2$, TFA, HCl 14.21 g (6 mM) of the preceding product in suspension in 80 ml of dichloromethane are treated in 10 mins. in an atmosphere of nitrogen by 120 ml of trifluoroacetic acid. After 45 mins. at ambient temperature with stirring, the product is concentrated in vacuo to ⅓ of the initial volume and is poured over 750 ml of stirred cold ether (+4° C.). The precipitate is filtered and washed with ether then dried in vacuo over potassium hydroxide then phosphoric anhydride. 13.9 g (97%) of product are obtained, used as such in the following reaction.

7.
Boc-Asp-(OBzl)-Ile-Met-Ser-Arg-Gln-Gln-Gly-Glu(OBzl)-Ser-Asn-Gln-Glu(OBzl)-Arg-Gly-Ala-Arg-Ala-Arg-Leu-NH$_2$, HCl 5.82 g (10 mM) of Boc-Asp(OBzl)-Ile-Met-NH-NH$_2$ in solution in 76.6 ml of DMF are treated between −20° and −25° with 6.66 ml (40 mM) of gaseous 6.0N HCl/dioxane, then with 1.45 ml (12 mM) of tertiobutyl nitrite in solution in 5 ml of DMF. After one hour between −20° and −25°, the product is neutralized to an apparent pH of 6-7 by addition of about 8 ml of diisopropylethylamine (DIPEA) and the total volume is adjusted to 100 ml with a little DMF, which leads to a 0.1 molar solution of azide (which is always conserved at around −20°).

13.84 g (about 5.8 mM) of the preceding TFA salt dissolved in 58 ml of DMSO and 87 ml of DMF are neutralized to an apparent pH of 6.7 with 1 ml of DIPEA and the solution thus obtained has 72.5 ml (or about 1.25 equiv.) of the above azide solution added thereto in about 10 mins. at a temperature of between −20° and −25°. The pH is adjusted to 6-7 by a little DIPEA and the solution conversed at −15°. After 16 hours, a further 14.5 ml (0.25 equiv.) of the azide solution is added. Monitoring by TLC shows a complete reaction after 24 hours, but reaction is stopped only after 40 hours by pouring the solution over 750 ml of stirred ice ethyl acetate.

The precipitate thus formed is filtered and washed abundantly with the same solvent and dried in vacuo in the presence of phosphoric anhydride. 14.35 g are thus obtained, used as such in the following step.

8.
H-Asp(OBzl)-Ile-Met-Ser-Arg-Gln-Gln-Gly-Glu(OBzl)-Ser-Asn-Gln-Glu(OBzl)-Arg-Gly-Ala-Arg-Ala-Arg-Leu-NH$_2$, TFA, HCl 14 g of the above product are stirred for 35 minutes in 80 ml of CH$_2$Cl$_2$+120 ml of TFA plus 10 ml HS(CH$_2$)$_2$SH. After concentration in vacuo by half, the reaction medium is poured over 800 ml of iced ether. The precipitate obtained is filtered, washed with ether then dried in vacuo over potassium hydroxide.

Yield: 100%.

9.
Boc-Gln-Asp(OBzl)-Ile-Met-Ser-Arg-Gln-Gln-Gly-Glu(OBzl)-Ser-Asn-Gln-Glu(OBzl)-Arg-Gly-Ala-Arg-Ala-Arg-Leu-NH$_2$, HCl

To the TFA salt obtained above (4.9 mM) dissolved in 120 ml of DMF plus 30 ml of DMSO and neutralized by NEM, are added 740 mg of HOBt (5.5 mM) then, in small portions, 2.02 g of Boc-Gln-ONp (5.5 mM), the pH of the reaction medium is maintained at around 6 by addition of NEM. After 6 hours, the reaction medium is poured in 800 ml of AcOEt. The precipitate obtained is filtered, washed with ethyl acetate, then with ether, then dried in vacuo.

Weight: 14.8 g—Yield: 100%.

The product is identified by NMR and AAA: Asp: 1.97-Ser: 2.0-Glu: 6.12-Gly: 2.06-Ala: 2.06-Met: 0.55-Ile: 0.93-Leu-0.99-Arg: 3.81-TLC: Rf 0.45-BPEW1

10.
H-Gln-Asp(OBzl)-Ile-Met-Ser-Arg-Gln-Gln-Gly-Glu(OBzl)-Ser-Asn-Gln-Glu(OBzl)-Arg-Gly-Ala-Arg-Ala-Arg-Leu-NH$_2$, TFA, HCl 14.7 of the above product are stirred for 35 mins. in 80 ml of CH$_2$Cl$_2$ plus 10 ml HS(CH$_2$)$_2$SH + 120 ml of TFA. After concentration in vacuo by half, the reaction medium is poured over 600 ml of iced ether. The precipitate obtained is filtered, washed with ether then dried in vacuo over potassium hydroxide.

Weight: 14.5 g.

11.
Boc-Arg-Lys(Z)-Leu-Leu-Gln-Asp(OBzl)-Ile-Met-Ser-Arg-Gln-Gln-Gly-Glu(OBzl)-Ser-Asn-Gln-Glu(OBzl)-Arg-Gly-Ala-Arg-Ala-Arg-Leu-NH$_2$, HCl

To the TFA salt obtained hereinabove (4.9 mM) dissolved in 120 ml of DMF plus 40 ml of DMSO and neutralized by NEM, 2.44 g of BOP (5.5 mM) and 4.2 g of Boc-Arg-Lys(Z)-Leu-Leu-OH, HCl (5.5 mM) are added in small portions in 30 mins. The pH of the reaction medium is maintained at around 6 by addition of NEM. After 23 hrs., the reaction medium is poured over one liter of AcOEt. The precipitate formed is filtered, washed with AcOEt then Et2O, then dried in vacuo.

M: 16.5 g—Yield: 93%—Product identified by NMR and AAA: Asp: 2.10-Ser: 1.86-Glu: 6.2-Gly: 2.00-Ala: 2.00-Met: 0.55-Ile: 0.80-Leu: 2.89-Lys: 0.87-Arg: 4.67-TLC Rf: 0.40 (BPEW1).

EXAMPLE XII

Synthesis of:
Boc-Ile-Phe-Asn-Thr-Ser-Tyr-Arg-Lys(Z)-Val-Leu-Gly-Gln-Leu-Ser-Ala-OH, HCl (peptide J)

1. H-Gln-Leu-Ser-Ala-OCH$_3$ 10.3 g (18.8 mM) of Boc-Gln-Leu-Ser-Ala-OCH$_3$ are stirred for 35 mins. in 100 ml of dichloromethane containing 100 ml of TFA. The reaction medium is concentrated in vacuo to about 50 ml and poured over 300 ml of ether. The precipitate is drained, washed with ether and dried in vacuo.

2.
Boc-Tyr-Arg(Z)-Val-Leu-Gly-Gln-Leu-Ser-Ala-OCH$_3$, HCl

To the TFA salt obtained hereinabove, dissolved in 200 ml of dimethylformamide and neutralized with N-ethylmorpholine are added 18.9 g (18.8 mM) of Boc-Tyr-Arg-Lys(Z)-Val-Leu-Gly-OH then 9.2 g of BOP (21 mM) then NEM to take the pH of the reaction medium to around 6. After 4 hrs. of stirring, the reaction medium is poured over 1 liter of AcOEt. The precipitate obtained is filtered, washed three times with 100 ml of AcOEt, then 3 times with 100 ml of Et2O then it is dried in vacuo.

24.16 g of product are obtained. Yield: 90% TLC Rf: 0.20 (BEW1)—alpha D: −17.6°—(Cc: 1-DMF with 5% AcOH)—Product identified by 1H NMR and AAA: Ser: 1.01-Glu: 0.99-Gly: 1.06-Ala: 1.01-Val: 0.98-Leu: 1.97-Tyr: 1.00-Lys: 0.98-Arg: 0.99-HPLC in reverse phase (EPP: 92%).

3.
H-Tyr-Arg-Lys(Z)-Val-Leu-Gly-Gln-Leu-Ser-Arg-OCH₃, HCl, TFA 8.66 g (6.1 mM) of the above product are stirred for 35 mins. in 37 ml of dichloromethane plus 3.5 ml of anisole plus 40 ml of TFA. After concentration in vacuo by half, the residue is poured over 300 ml of iced ether; the white precipitate obtained is filtered, washed with ether then dried in vacuo over potassium hydroxide.
Weight: 8.68 g—Yield: 100%.

4. Boc-Ile-Phe-Thr-Asn-Ser-N₃

5.94 g (8.55 mM) of Boc-Ile-Phe-Thr-Asn-Ser-NH-NH₂ are dissolved in 27 ml of DMSO plus 37 ml of DMF. After cooling to −25° C., 6.1 ml of a 5.6 N HCl/dioxane solution then 1.23 ml of tertiobutyl nitrite (1.2 equiv.) prediluted in 5 ml of DMF precooled to −20° C., are added. After 1 hr. 15 mins. of stirring between −20° and −25° C., 6.1 ml of diisopropylethylamine (DIPEA) are added to take the pH to around 6, then 3 ml of DMF are added to take the volume to 85 ml and this solution is conserved at −25° C.

5.
Boc-Ile-Phe-Thr-Asn-Ser-Tyr-Arg-Lys(Z)-Val-Leu-Gly-Gln-Leu-Ser-Ala-OCH₃, HCl

The TFA salt obtained in Example XI-3 is dissolved in 70 ml of DMF and neutralized by DIPEA then added in 15 mins. to 70 ml of the azide solution obtained hereinabove at −20° C. Then DIPEA is added to take the pH towards 7, the product is stirred for one hour at −20° C., then the medium is conversed at −12° C. After 22 hrs., 5 ml of the azide solution are added and the pH is raised towards 7 by DIPEA. After 45 hrs., the remaining azide solution is added and the pH is raised towards 7 by DIPEA. After 74 hrs., the reaction medium is poured over 1200 ml of ethyl acetate. The white precipitate obtained is filtered, washed with ethyl acetate then with ether, then dried in vacuo.
Weight: 10.46 g—Yield: 86%.

By concentration of the mother liquors and reprecipitation by an ethyl acetate/ether mixture, a second jet is obtained which makes it possible to have an overall yield of 95%. The coupling product is identified by 1H NMR and AAA: Asp: 1.02-Thr: 1.03-Ser: 1.91-Glu: 0.97-Gly: 1.06-Ala: 1.06-Val: 1.00-Ile: 0.94-Leu: 1.98-Tyr: 1.04-Phe: 1.02-Lys: 0.94-Arg: 1.02-TLC Rf: 0.20 (BEW1)—HPLC in reverse phase (EPP: 90%).

6.
Boc-Ile-Phe-Thr-Asn-Ser-Tyr-Arg-Lys(Z)-Val-Gly-Gln-Leu-Gly-Gln-Leu-Ser-Ala-OH, HCl 5.3 g (2.7 mM) of the product obtained hereinabove are dissolved in 40 ml of DMSO plus 6 ml of water; 10 ml of 1N sodium hydroxide are added drop by drop, the product is stirred for 30 mins. then neutralized with 10 ml of 1N hydrochloric acid. The reaction medium is poured over one liter of ethyl acetate. The precipitate obtained is filtered, washed 4 times with ethyl acetate then twice with water, then 4 times with ether, then it is dried in vacuo over P₂O₅.
Weight: 4.56 g—Yield: 86%—Product identified by 1H NMR and AAA—TLC: Rf: 0.5 BEW1.

EXAMPLE XIII

Synthesis of
Z-Tyr-Ala-Asp(OBzl)-Ala-Ile-Phe-Thr-Asn-Ser-Tyr-Arg-Lys(Z)-Val-Leu-Gly-Gln-Leu-Ser-Ala-Arg-Lys(Z)-Leu-Leu-Gln-Asp(OBzl)-Ile-Met-Ser-Arg-Gln-Gln-Gly(OBzl)-Ser-Asn-Gln-Glu(OBzl)-Arg-Gly-Ala-Arg-Ala-Arg-Leu-NH₂, HCl (GRF 1-44 protected)

1.
H-Arg-Lys(Z)-Leu-Leu-Gln-Asp(OBzl)-Ile-Met-Ser-Arg-Glu-Gln-Gly-Glu(OBzl)-Ser-Asn-Gln-Glu(OBzl)-Arg-Gly-Ala-Arg-Ala-Arg-Leu-NH₂, HCl, TFA 1.4 g of the product of Example X-11 are stirred for 35 mins. in 60 ml of CH₂Cl₂, plus 70 ml of TFA+7 ml of ethane dithiol. After concentration in vacuo by half, the residue is poured over 500 ml of ice ether. The precipitate obtained is filtered, washed with ether, then dried in vacuo over potassium hydroxide. (Weight: 7.44 g).

2.
Boc-Ile-Phe-Thr-Asn-Ser-Tyr-Arg-Lys(Z)-Val-Leu-Gly-Gln-Leu-Ser-Ala-Arg-Lys(Z)-Leu-Leu-Gln-Asp(OBzl)-Ile-Met-Ser-Arg-Gln-Gln-Gly-Glu(OBzl)-Ser-Asn-Gln-Glu(OBzl)-Arg-Gly-Ala-Arg-Ala-Arg-Leu-NH₂, HCl

To 6.6 g of the above TFA salt (1.9 mM) dissolved in 36 ml of DMSO plus 90 ml of DMF and neutralized by NEM, 1.0 g of BOP (2.3 mM) then 3.8 g of the peptide of Example XI-6 (1.9 mM) are added, the pH of the reaction medium is taken to 6 with NEM. After 19 hours, 1.15 mM of BOP are added. After 26 hrs., the reaction medium is poured over 600 ml of AcOEt. The precipitate obtained is filtered, washed with AcOEt, then filtered and dried in vacuo. Yield: 88% (9.2 g)—product identified by NMR and AAA.

3.
H-Ile-Phe-Thr-Asn-Ser-Tyr-Arg-Lys(Z)-Val-Leu-Gly-Gln-Leu-Ser-Ala-Arg-Lys(Z)-Leu-Leu-Gln-Asp(OBzl)-Ile-Met-Ser-Arg-Gln-Gln-Gly-Glu(OBzl)-Ser-Asn-Gln-Glu(OBzl)-Arg-Gly-Ala-Arg-Ala-Arg-Leu-NH₂, HCl, TFA 9.1 g of the above product are stirred for 35 mins. in 100 ml of TFA plus 5 ml of ethane dithiol. The reaction medium is then poured over 500 ml of iced ether. The precipitate obtained is filtered, washed with Et2O, then dried in vacuo over potassium hydroxide.
Yield: 100%.

4. Protected GRF-1-44

To 9.10 g of the preceding TFA salt (1.66 mM) in solution in 50 ml of DMF and 50 ml of DMSO and neutralized by NEM, are added 1.18 g of the peptide described in Example IX-3 (1.78 mM) and 0.79 g of BOP (1.78 mM); the pH is maintained at around 6 by NEM. After 23 hrs. at ambient temperature, the reaction medium is poured over 600 ml of AcOEt. The precipitate formed is filtered, washed with ethyl acetate, then with ether and finally dried in vacuo.
Yield: 8.54 g (84%), Monitored by NMR and TLC:-AAA: Asp: 4.2-Thr: 0.92-Ser: 4.02-Glu: 7.37 (for 7)-Gly: 3.14 (for 3)-Ala: 5.11-Val: 1.01-Met: 0.61-Ile: 1.84-Leu: 4.98-Tyr: 1.87-Phe: 0.95-Arg: 5.90.

EXAMPLE XIV

Deprotection of GRF 1-44

4.5 g of the product obtained in accordance with Example XII-4 are stirred for one hour at 0° in 180 ml of TFA containing 19.8 ml of TFMSA, 27 ml of thioanisole and 11 of metacresol. 1 l. of ether is then added. The precipitate obtained is filtered, washed with ether then dried one hour in vacuo in the presence of potassium hydroxide. The product is redissolved in 200 ml of water and ion exchanger resin Amberlite IR 45 (in the form of acetate) is added in order to return the pH to 4.5. The medium is stirred for 30 mins. at ambient temperature. The resin is filtered, washed with water and the filtrates concentrated to 50 ml then lyophilized. Yield: 3.85 g. Monitored by NMR of the disappearance of the protector groups Z and OBzl.

TLC (BEPW1): majority spot Rf 0.38.

EXAMPLE XV

Purification of the GRF 1-44

The deprotected peptide obtained in the preceding Example (XIII) is subjected to a chromatography over Sephadex G 50 gel (fine), using 30% acetic acid as eluent.

The fractions containing the expected peptide are collected together, evaporated and lyophilized.

The lyophilizate thus obtained is purified in turn by a chromatography over a cation exchanger of the CM-32 carboxymethylcellulose (Whatman) type, using a linear gradient of ammonium acetate of between 01M (pH 4.5) and 0.4M (pH 6.5). For example, for 1 charge of 1 g of peptides to be purified, a chromatography column having a bed volume of about 50 ml for a height of 20 cm will be used.

The fractions containing the peptide with a degree of purity $\geq 80\%$ (HPLC) are collected together and lyophilized up to constant weight (in order to eliminate the $CH_3CO_2NH_4$) buffer.

Finally, the preceding lyophilizate is subjected to a partition chromatography, using as support of the stationary liquid phase, fine Sephadex G 50 and with the aid of the following system of solvents: n-butanol/ethanol/pyridine/0.2N acetic acid in the proportion of 4/1/1/7 (in volume). The fractions of chromatography are monitored by HPLC and those of which the titer of purity is $\geq 95\%$ are collected together and lyophilized.

The product is finally monitored by analysis of the amino acids:

Tyr: 1.91 (2)
Ala: 4.88 (5)
Aln, Asp: 3.86 (4)
Ile: 1.96 (2)
Phe: 0.93 (1)
Thr: 1.02 (1)
Ser: 3.88 (4)
Arg: 5.89 (6)
Lys: 1.98 (2)
Val: 1.01 (1)
Leu: 5.10 (5)
Gly: 2.98 (3)
Gln, Glu: 6.82 (7)
Met: 0.91 (1)

EXAMPLE XVI

Synthesis of Boc-Glu-Ser-Asn-Gln-Glu-Arg-Gly (fragment B)

1-Z-Arg(NO2)-Gly-OBzl 353 g of tosylate of glycine benzyl ester (H-Gly-o-Bzl, Tosylate) are dissolved in 2 liters of DMF; 115 g of NEM then 353 g of Z-Arg($NO_2$)-OH and finally 500 g of BOP are added. The pH of the medium is adjusted to 7 with the aid of NEM and using pH indicating paper on samples of the reaction medium diluted with water. The reaction medium is stirred and the state of advance of the reaction followed by TLC. After 4 hrs., the reaction is complete and the medium evaporated to dryness in vacuo at 35°. The residue of evaporation is taken up in 2 liters of ethyl acetate and 2 liters of water. Under these conditions, a solid is obtained which is drained and washed successively in solid phase with a 5% aqueous solution of $HKSO_4 + K_2SO_4$, with pure water, with a 5% aqueous solution of $NaHCO_3$ and finally water.

The product is dried in air and monitored by NMR and TLC.

Yield: 410 g (82%).

2. H-Glu(OBzl)-Arg-Gly-OH 500 g of the preceding product in solution in 3 liters of HClN in DMF and in the presence of 100 g of Pd/C with 10% of Pd are hydrogenated under a pressure of 1.5 bar of hydrogen. After 24 hours, the reaction is terminated (monitored by TLC). The catalyst is filtered and the pH of the medium adjusted to 7 by addition of N-ethyl morpholine and using pH indicating paper on samples diluted with water. 458 g of Boc-Glu(OBzl)-O Np are introduced in solution in 1 liter of DMF. The reaction medium is diluted by addition of 1 liter of water and 135 g of OHBT and NEM are progressively added in sufficient quantities to maintain the pH at 7.

The medium is stirred for 4 hours at ambient temperature. One makes sure that the reaction is complete and the solvent is evaporated in vacuo at the temperature of 35°. The residue of evaporation is taken up in ethyl acetate. Under these conditions, the product becomes solid. It is drained and chromatographed over silica gel, using chloroform-methanol (70-30 by volume) as eluent. Evaporation of the fractions of chromatography containing the pure product leads to 412 g (75%) of a white powdery compound after lyophilization. It is monitored by TLC and NMR.

The preceding product is dissolved at ambient temperature in 3 liters of a (50/50) mixture of TFA and $CH_2Cl_2$. The medium is maintained for 15 mins. at ambient temperature, and is evaporated to dryness in vacuo, maintaining the temperature at 20°. The residue is taken up in ethyl ether and the solid obtained is drained and dried. The yield is 423 g (100%) in the form of trifluoroacetate.

3. H-Gln-Glu(OBzl)-Arg-Gly-OH 564 g of trifluoroacetate of H-Glu(OBzl)-Arg-Gly-OH are dissolved in 3 liters of dimethyl formamide. The pH is adjusted to 7 by addition of NEM on samples diluted with water and with the aid of pH indicating paper.

367 g of Boc-Gln-ONp arethen introduced in solution in 1 liter of DMF. The reaction medium is diluted by addition of 1 liter of water. 135 g of OHBT and the sufficient quantity of NEM for the pH to be maintained at 7 are progressively added.

The mixture is stirred for 4 hours at ambient temperature. The end of the reaction is monitored by TLC and the solvent is evaporated in high vacuum at 35°. The residue of evaporation is triturated in ethyl acetate. Under these conditions, a hygroscopic solid is obtained which is used as such for the treatment with trifluoroacetic acid—$CH_2Cl_2$ (2 liters of the 50-50 by volume mixture).

The medium is conserved for 10 minutes at ambient temperature and finally evaporated in vacuo at 20°. The residue of evaporation is triturated in ethyl ether to yield 525 g (76%) of H-Gln-Glu(OBzl)-Arg-Gly-OH. (Monitored by NMR and TLC).

4. H-Asn-Gln-Glu(OBzl)-Arg-Gly-OH

By using the conditions of Example II-2 strictly and from H-Gln-Glu(OBzl)-Arg-Gly-OH, trifluoroacetate (691 g) and 393 g of Boc-Asn-ONb, 685 g (85%) of a solid white product are obtained, monitored by NMR and TLC.

5. H-Ser-Asn-Gln-Glu(OBzl)-Arg-Gly-OH

Likewise under the conditions of Example II-2 and from 806 g of H-Asn-Gln-Glu(OBzl)-Arg-Gly-OH and 366 g of Boc-Ser-ONb, the product is obtained, monitored by NMR and TLC with a yield of 688 g (77%) and in trifluoroacetate form.

6. Boc-Glu(OBzl)-Ser-Asn-Gln-Glu(OBzl)-Arg-Gly-OH (fragment B)

From 894 g of H-Ser-Asn-Gln-Glu(OBzl)-Arg-Gly-OH trifluoroacetate and 458 g of Boc-Glu(OBzl)-ONp are obtained 824 g (80%) of the expected product after purification by crystallization in the DMF-ether (50-50 by volume) medium.

The product is monitored by NMR, TLC and analysis of amino acids:
Gln-Glu: 2.92 (3)
Ser: 0.97 (1)
Asn: 1.03 (1)
Arg: 0.97 (1)
Gly: 0.96 (1)

By following the strategies presented in Tables V, VI, VII and VIII and the techniques described in Examples I to IX and XVI, the following compounds may be obtained:
Boc-Lys(Z)-Leu-Leu-Gln-OH (fragment E)
Boc-Gln-Leu-Ser-Ala-Arg-OH (fragment F)
Boc-Lys(Z)-Val-Leu-Gly-OH (fragment G)
Boc-Ile-Phe-Thr-Asn-Ser-Tyr-Arg-OH (fragment H)

EXAMPLE XVII

Boc-Glu(OBzl)-Ser-Asn-Gln-Glu(OBzl)-Arg-Gly-Ala-Arg-Ala-Arg-Leu-NH₂ (fragment B-A)

69.2 g of fragment A hydrochloride are dissolved in 500 ml of DMF. The pH is adjusted to 7 on samples diluted with water and with the aid of pH indicating paper and NEM. 117 g of fragment B, 55 g of BOP are then added, the pH is again adjusted to 7 with the aid of NEM and the medium is stirred for 14 hours at ambient temperature. After monitoring the end of reaction by TLC, 2 liters of ethyl ether are added to the reaction medium. A white powdery precipitate is deposited under these conditions. It is purified by recrystallization in DMF-ethyl acetate. The drained product is then washed with ethyl acetate in solid phase and dried.

149 g (81%) of a white product are obtained, monitored by TLC and NMR. Analysis of amino acids:
Gln-Glu: 2.92 (3)
Ser: 1.02 (1)
Asn: 0.97 (1)
Arg: 2.89 (3)
Gly: 1.01 (1)
Ala: 1.98 (2)
Leu: 0.93 (1)

DEPROTECTION OF N-TERMINAL NITROGEN

The product described in the preceding Example (184 g) is introduced in a mixture constituted by 750 ml of TFA and 750 ml of $CH_2Cl_2$ with stirring and at ambient temperature. After dissolution, the mixture is conserved for 15 mins. at the same temperature and evaporated in vacuo, maintaining the medium of evaporation at 25°. The residue of evaporation is triturated in ether and, under these conditions, a white powdery solid is obtained, which is dried in vacuo and monitored by TLC and NMR.

The following compounds may be obtained in accordance with the techniques of Example XVII and representing the different stages of elongation of the peptide.

Fragment: C-B-A
Boc-Ser-Arg-Gln-gln-Gly-Glu(OBzl)-Ser-Asn-Gln-Glu-(H) Arg-Gly-Ala-Arg-Ala-Arg-Leu-NH₂

Fragment: D—C—B—A

Boc—Asp—Ile—Met—Ser—Arg—Gln— (OBzl above Asp)
Gln—Gly—Glu(OBzl)—Ser—(H)
Asn—Gln—Glu(OBzl)—Arg—Gly—
Ala—Arg—Ala—Arg—Leu—NH₂

In this particular case, fragment D is introduced, using the activation of the azides

As soon as the methionine is in sequence, a scavenger will be used in the course of the different treatments by TFA-$CH_2Cl_2$ during the phases of selective deprotection (elimination of the Boc). The invention recommends thioanisole as agent for protecting the methionine from oxidation in the proportion of 5% in the TFA-$CH_2Cl_2$ medium.

Fragment: E-D-C-B-A
Boc-Lys(Z)-Leu-Leu-Gln-Asp(OBzl)-Ile-Met-Ser-Arg-Gln (H) Gln-Gly-Glu(OBzl)-Ser-Asn-Gln-Glu(OBzl)-Arg-Gly-Ala-Arg-Ala-Arg-Leu-NH₂

Fragment: F-E-D-C-B-A
Boc-Gln-Leu-Ser-Ala-Arg-Lys(Z)-Leu-Leu-Gln-Asp(OBzl) (H) Ile-Met-Ser-Arg-Gln-Gln-Gly-Glu(OBzl)-Ser-Asn-Gln-Glu(OBzl)-Arg-Gly-Ala-Arg-Ala-Arg-Leu-NH₂

Fragment: G-F-E-D-C-B-A
Boc-Lys(Z)-Val-Leu-Gly-Gln-Leu-Ser-Ala-Arg-Lys(Z)-Leu-Leu-Ser-Asp(OBzl)-Ile-Met-Ser-Arg-Gln-Gln-Gly-Glu(OBzl)-Ser-Asn-Gln-Glu(OBzl)-Arg-Gly-Ala-Arg-Ala-Arg-Leu-NH₂

Fragment: H-G-F-E-D-C-B-A

Boc-Ile-Phe-Thr-Asn-Ser-Tyr-Arg-Lys(Z)-Val-Leu-(H)-Gly-Gln-Leu-Ser-Ala-Arg-Lys(Z)-Leu-Leu-Gln-Asp(OBzl)-Ile-Met-Ser-Arg-Gln-Gln-Gly-Glu(OBzl)-Ser-Asn-Gln-Glu(OBzl)-Arg-Gly-Ala-Arg-Ala-Arg-Leu-NH$_2$ protected hPGRF Z-Tyr-Ala-Asp(OBzl)-Ala-Ile-Phe-Thr-Asn-Ser-Tyr-Arg-Lys(Z)-Val-Leu-Gly-Gln-Leu-Ser-Ala-Arg-Lys(Z)-Leu-Leu-Gln-Asp(OBzl)-Ile-Met-Ser-Arg-Gln-Gln-Gly-Glu(OBzl)-Ser-Asn-Gln-Glu(OBzl)-Arg-Gly-Ala-Arg-Ala-Arg-Leu-NH$_2$ Deprotection and purification of the hpGRF-1-44 are then carried out as indicated in Examples XIV and XV.

What is claimed is:

1. A process for the synthesis, in liquid phase and by fragments, of hpGRF 1-44 and hpGRF 1-40, comprising the steps of:

coupling, one after the other and in the order of the sequence of the GRF, the following fragments:

H-Ala-Arg-ala-Arg-Leu-NH$_2$ (40-44), called fragement A or alaninamide;

Boc-Glu(OBzl)-Ser-Asn-Gln-Glu(OBzl)-Arg-Gly-OH (33-39), called fragment B;

Boc-Ser-Arg-Gln-Gln-Gly-OH (28-32), called fragment C;

Boc-Asp(OBzl)-Ile-Met-NH-NH$_2$ (25-27), called fragment D;

Boc-Lys(Z)-Leu-Leu-Gln-OH (21-24), called fragment E;

Boc-Gln-Leu-Ser-Ala-Arg-OH (16-20), called fragment F;

Boc-Lys(Z)-Val-Leu-Gly-OH (12-15), called fragment G;

Boc-Ile-Phe-Thr-Asn-Ser-Tyr-Arg-OH (5-11), called fragment H; and

Z-Tyr-Ala-Asp(OBzl)-Ala-OH (1-4), called fragment I;

wherein (a) the side acid functions of the aspartic and glutamic acids and the side amine function of the lysine are protected by protector groups stable under the conditions of deprotection of the group Boc, (b) the guanidine function of the arginine is protected by protonation, and (c) the N-terminal amino acid is protected on the amine by the Boc group;

selectively eliminating the group Boc from the N-terminal amine of the peptide in phase of elongation by hydrolysis with trifluoroacetic acid, said coupling being effected in an aprotic polar solvent; and eliminating, at the end of the sequence, all the protector groups by hydrolysis with the aid of a 0.1 to 1M solution of methanesulfonic or trifluoromethanesulfonic acid in trifluoroacetic acid.

2. The process of claim 1, wherein, after each coupling, the product obtained is isolated from the reaction medium by precipitation with the aid of an apolar solvent.

3. The process of claim 1, wherein the crude product of reaction is purified by counter-current distribution and permeation chromatography over gel.

4. The process of claim 1, wherein alaninamide is used in place of fragment A and the peptide obtained is hpGRF 1-40.

5. The process of claim 1, wherein the following three peptide fragments are coupled successively and in the order of the sequence of the GRF:

(1) H-Arg-Lys(Z)-Leu-Leu-Gln-Asp(OBzl)-Ile-Met-Ser-Arg-Gln-Gln-Gly-Glu(OBzl)-Ser-Asn-Gln-Glu(OBzl)-Arg-Gly-Ala-Arg-Ala-Arg-Leu-NH$_2$ (sequence 20-44 of the GRF, called peptide K)

(2) Boc-Ile-Phe-Thr-Asn-Ser-Tyr-Arg-Lys(Z)-Val-Leu-Gly-Gln-Leu-Ser-Ala-OH (sequence 5-9 of the GRF called peptide J);

(3) Z-Tyr-Ala-Asp(OBzl)-Ala-OH (sequence 1-4 of the GRF called peptide I);

said peptide obtained being hpGRF 1-44.

6. The process of claim 5, wherein the peptide fragment corresponding to sequence 20-40 of the GRF is used in place of the peptide K, said peptide obtained being hpGRF 1-40.

7. The process of claim 1, wherein the coupling is carried out with the aid of the hexafluorophosphate of benzotriazolyloxyphosphonium (BOP) or dicyclohexylcarbodiimide in the presence of 1-hydroxy benzotriazole (coupling agent) or by activation with carboxyazides, in dimethylformamide or dimethylsulfoxide.

* * * * *